(12) United States Patent
Kwon et al.

(10) Patent No.: US 9,371,286 B2
(45) Date of Patent: Jun. 21, 2016

(54) PHARMACEUTICAL COMPOSITION WITH ENHANCED EFFICACY FOR INHIBITING ANGIOGENESIS

(75) Inventors: Ho Jeong Kwon, Seoul (KR); Gyoon Hee Han, Gyeonggi-do (KR); Hye Jin Jung, Seoul (KR); Jeong Jea Seo, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 111 days.

(21) Appl. No.: 14/232,598

(22) PCT Filed: May 23, 2011

(86) PCT No.: PCT/KR2011/003773
§ 371 (c)(1),
(2), (4) Date: Jul. 6, 2014

(87) PCT Pub. No.: WO2012/124858
PCT Pub. Date: Sep. 20, 2012

(65) Prior Publication Data
US 2014/0315947 A1    Oct. 23, 2014

(30) Foreign Application Priority Data
Mar. 16, 2011 (KR) .................. 10-2011-0023211

(51) Int. Cl.
*C07D 215/38* (2006.01)
*C07C 311/21* (2006.01)
*C07C 311/20* (2006.01)

(52) U.S. Cl.
CPC ............ *C07D 215/38* (2013.01); *C07C 311/20* (2013.01); *C07C 311/21* (2013.01); *C07C 2101/14* (2013.01)

(58) Field of Classification Search
CPC .. C07D 215/38; C07C 311/20; C07C 311/21; C07C 2104/14
See application file for complete search history.

(56) References Cited

U.S. PATENT DOCUMENTS

2008/0064714 A1*    3/2008    Vennemann et al. ......... 514/294

FOREIGN PATENT DOCUMENTS

| JP | 11-184056 A | | 7/1999 |
| KR | 10-2009-0010979 A | | 1/2009 |
| WO | 2007031608 | * | 3/2007 |
| WO | 2007076055 | * | 7/2007 |
| WO | 2007-135080 A2 | | 11/2007 |
| WO | 2009143024 | * | 11/2009 |
| WO | 2010010154 | * | 1/2010 |

OTHER PUBLICATIONS

Semenza, Nature Reviews, vol. 3, 721-732, Oct. 2003.*
International Search Report for PCT/KR2011/003773.
Jennifer A. Jacobsen et al., "Identifying Chelator for 11 Metalloprotein Inhibitors Using a Fragment-Based Approach", Journal of Medicinal Chemistry, (Dec. 28, 2010), Vol.54, pp. 591-602.
Hye Jin Jung et al., "Identification of a novel small molecule targeting UQCRB of mitochondrial complex III and its anti-angiogenic activity", Bioorganic & Medicinal Chemistry Letters 21 (2011) 1052-1056.
Hye Jin Jung et al., "Terpestacin Inhibits Tumor Angiogenesis by Targeting UQCRB of Mitochondrial Complex III and Suppressing Hypoxia-induced Reactive Oxygen Species Production and Cellular Oxygen Sensing", The Journal of Biological Chemistry vol. 285, No. 15, pp. 11584-11595, Apr. 9, 2010.

* cited by examiner

*Primary Examiner* — D M Seaman
(74) *Attorney, Agent, or Firm* — Harness, Dickey & Pierce, P.L.C.

(57) ABSTRACT

The present invention relates to a pharmaceutical composition for inhibiting angiogenesis and a novel sulfonyl amide derivative compound which can be useful for the prevention or treatment of angiogenesis-related diseases or disorders. Since the compound used as an active ingredient in the pharmaceutical composition of the invention is specifically bound to UQCRB and inhibits biological functions thereof, apoptosis is not induced and angiogenic responses are inhibited. Therefore, the compound used as an active ingredient in the pharmaceutical composition of the invention can be useful as an effective and safe angiogenesis inhibitory agent.

10 Claims, 5 Drawing Sheets

PHARMACEUTICAL COMPOSITION WITH ENHANCED EFFICACY FOR INHIBITING ANGIOGENESIS

CROSS REFERENCE TO RELATED APPLICATIONS AND CLAIM OF PRIORITY

This patent application is a National Phase application under 35 U.S.C. §371 of International Application No. PCT/KR2011/003773, filed 23 May 2011, which claims priority to Korean Patent Application number 10-2011-0023211, filed 16 Mar. 2011, entire contents of which are incorporated herein by reference.

BACKGROUND

1. Technical Field

The present invention relates to a pharmaceutical composition for inhibiting angiogenesis, the composition containing, as an effective ingredient, a novel synthetic low-molecular compound targeting ubiquinol-cytochrome c reductase binding protein (UQCRB).

2. Description of the Related Art

Angiogenesis is a key process for progression of many solid tumors. Accordingly, the efficient inhibition of angiogenesis is considered to be a powerful way to suppress tumor growth and metastasis. Consequently, several specific target proteins of angiogenesis, including vascular endothelial growth factor receptors (VEGFs), matrix metalloproteinases, aminopeptidases, histone deacetylases, and calmodulin, have been identified and anti-angiogenic agents of various scaffolds have been developed based on their inhibitory activities toward the specific targets. We recently isolated terpestacin, a new angiogenesis inhibitor with a unique bicyclo sesterterpene structure, from fungal metabolites. To investigate the molecular mechanism of terpestacin regarding its anti-angiogenic activity, we identified a cellular binding protein of terpestacin using a reverse chemical proteomics approach. Terpestacin specifically bound to the 13.4-kDa subunit (UQCRB) of complex III in the mitochondrial respiratory chain. Recent reports have suggested that reactive oxygen species (ROS) generation at mitochondrial complex III triggers hypoxia-inducible factor-1a (HIF-1a) stabilization during hypoxia. Indeed, terpestacin binding to UQCRB inhibited hypoxia-induced ROS generation, leading to inhibition of HIF-1a and tumor angiogenesis in vivo, without disrupting mitochondrial respiration and complex III functional structure. In addition, the regulation of UQCRB expression demonstrated that the protein is a critical mediator of hypoxia-induced tumor angiogenesis via mitochondrial ROS-mediated signaling. This discovery suggested that small molecules targeting UQCRB in mitochondrial complex III can suppress tumor angiogenesis without acting as a respiratory poison. As such, we attempted to develop new small molecules that specifically regulate the function of UQCRB.

Throughout the specification, a number of publications and patent documents are referred to and cited. The disclosure of the cited publications and patent documents is incorporated herein by reference in its entirety to more clearly describe the state of the related art and the present disclosure.

SUMMARY

The present inventors endeavored to develop an anti-angiogenesis agent for effectively inhibiting angiogenesis without cytotoxicity. As a result, the present inventors found a novel synthetic low-molecular compound targeting ubiquinol-cytochrome c reductase binding protein (UQCRB) of mitochondrial complex III, as a new molecular target for angiogenesis, and confirmed that this compound binds to UQCRB to effectively inhibit angiogenesis, based on which the present inventors completed the present invention.

Accordingly, an aspect of the present invention is to provide a pharmaceutical composition for inhibiting angiogenesis.

Another aspect of the present invention is to provide a novel sulfonyl amide derivative compound.

Still another aspect of the present invention is to provide a method for prevention or treatment of uncontrolled angiogenesis-related diseases or disorders.

Other purposes and advantages of the present invention will become clarified by the following detailed description of invention, claims, and drawings.

In accordance with an aspect of the present invention, there is provided a pharmaceutical composition for inhibiting angiogenesis, the pharmaceutical composition including, as an effective ingredient, a compound represented by Chemical Formula 1 below:

Chemical Formula 1

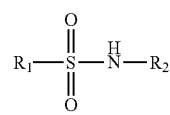

wherein, $R_1$ is

($A_1$ is straight chain or branched chain $C_1$-$C_6$ alkyl, phenyl substituted with unsubstituted or straight chain or branched chain $C_1$-$C_6$ alkyl or halogen), or naphthalyl substituted with unsubstituted or straight chain or branched chain $C_1$-$C_6$ alkyl; and $R_2$ is

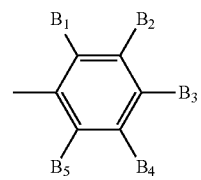

($B_1$ to $B_5$ each are independently hydrogen, halogen, hydroxy, nitro, or $C_1$-$C_6$ alkyl), hydroxy naphthalyl, 4-hydroxybenzyl $C_1$-$C_3$ alkyl, 4-(2-hydroxyethyl)cyclohexyl, or quinoline substituted with unsubstituted or straight chain or branched chain $C_1$-$C_6$ alkyl, halogen, or hydroxy.

In accordance with another aspect of the present invention, there is provided a method for prevention or treatment of uncontrolled angiogenesis-related diseases or disorders, the method including administering the pharmaceutical composition to a subject in need thereof.

According to a preferable embodiment of the present invention, $A_1$ of $R_1$ in Chemical Formula 1 of the present invention is methyl, ethyl, phenyl, or tert-butyl.

According to a preferable embodiment of the present invention, $B_1$ of $R_2$ in Chemical Formula 1 of the present invention is hydrogen, chloride, fluoro, hydroxy, nitro, or methyl.

According to a preferable embodiment of the present invention, hydroxy naphthalyl of $R_2$ in Chemical Formula 1 of the present invention is 7-hydroxy naphthalyl.

According to a preferable embodiment of the present invention, quinoline of $R_2$ in Chemical Formula 1 of the present invention is 8-hydroxy quinoline.

According to a preferable embodiment of the present invention, the compound of the present invention is selected from the group consisting of compounds represented by Chemical Formulas 2 to 29 below.

Chemical Formula 2

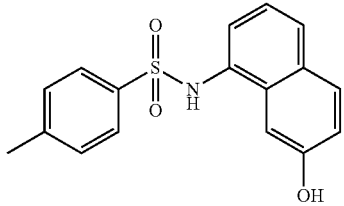

Chemical Formula 3

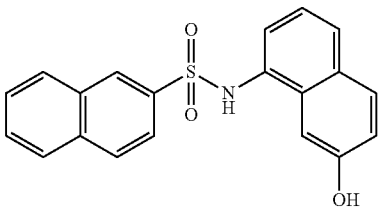

Chemical Formula 4

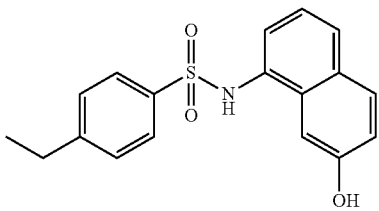

Chemical Formula 5

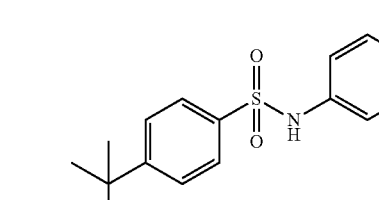

Chemical Formula 6

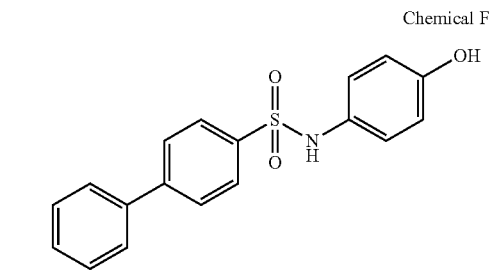

-continued

Chemical Formula 7

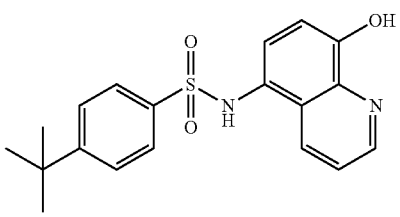

Chemical Formula 8

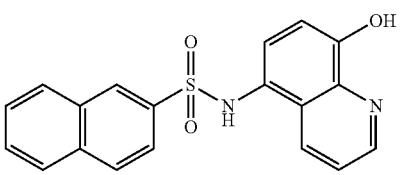

Chemical Formula 9

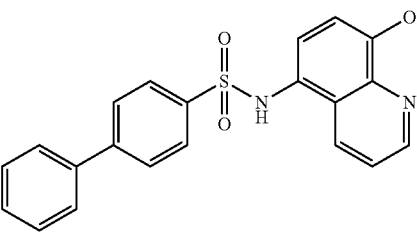

Chemical Formula 10

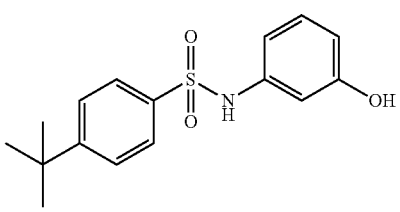

Chemical Formula 11

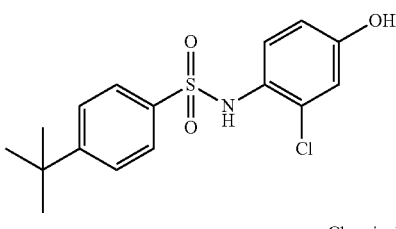

Chemical Formula 12

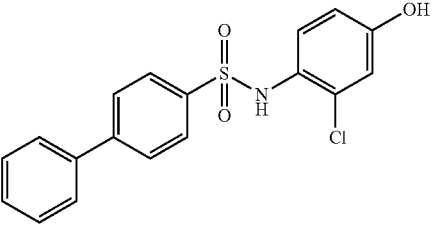

Chemical Formula 13

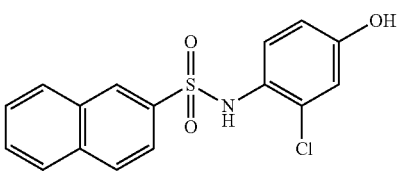

Chemical Formula 14
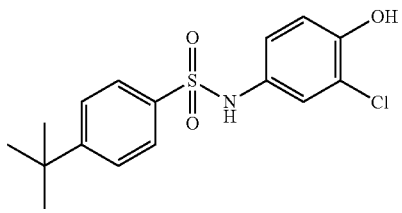
Chemical Formula 15
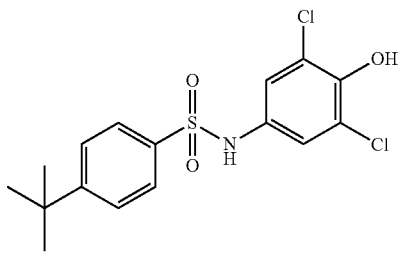
Chemical Formula 16
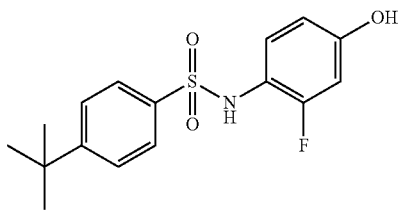
Chemical Formula 17
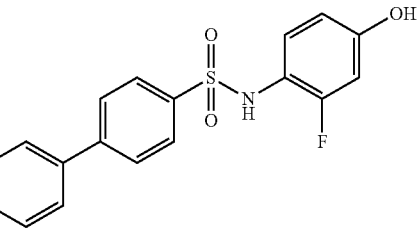
Chemical Formula 18
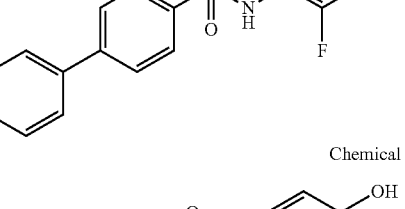
Chemical Formula 19
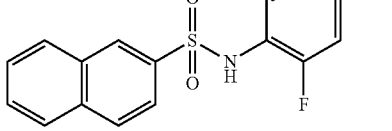
Chemical Formula 20
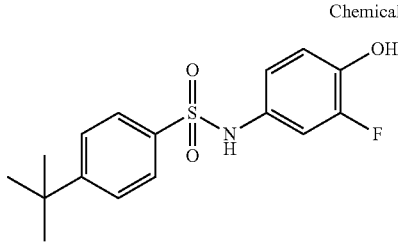
Chemical Formula 21
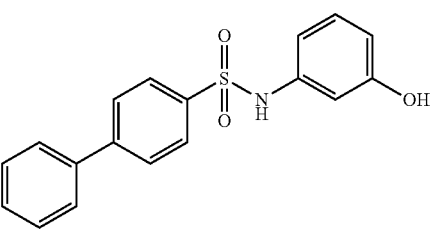
Chemical Formula 22
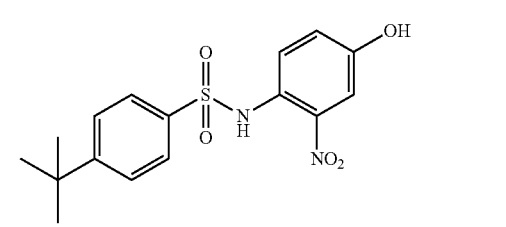
Chemical Formula 23
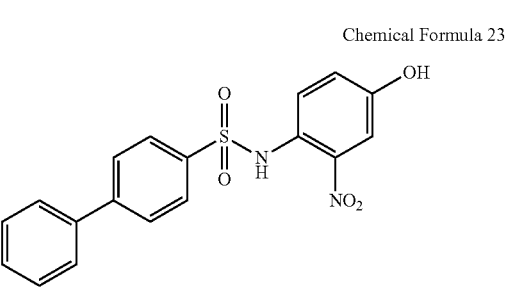
Chemical Formula 24
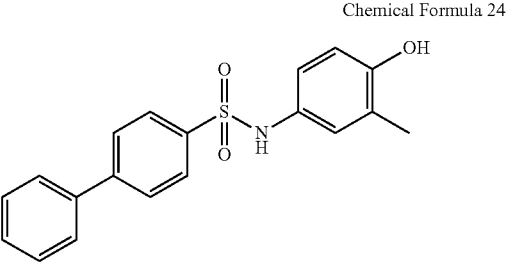
Chemical Formula 25
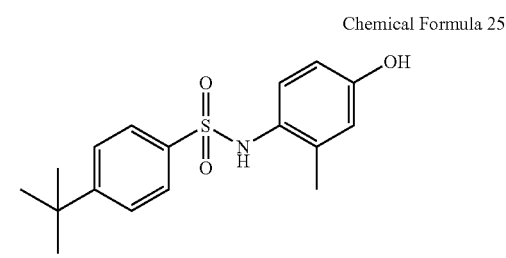
Chemical Formula 26
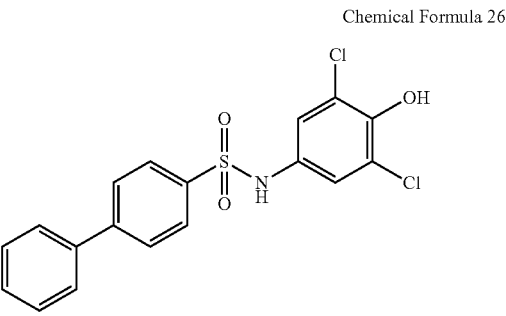

Chemical Formula 27

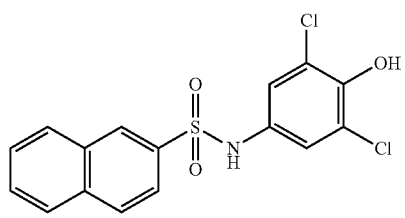

Chemical Formula 2

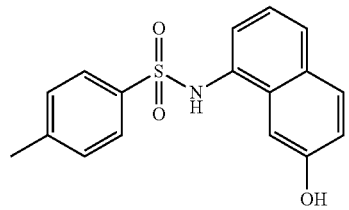

Chemical Formula 28

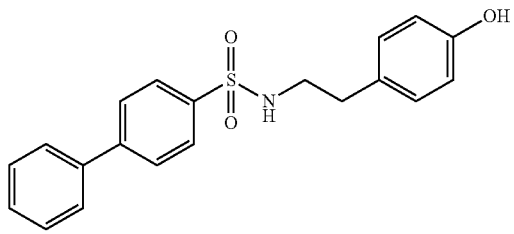

Chemical Formula 3

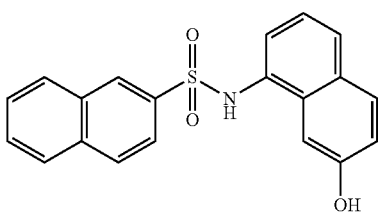

Chemical Formula 29

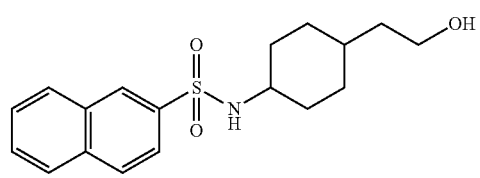

Chemical Formula 4

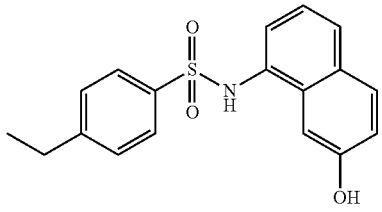

Chemical Formula 8

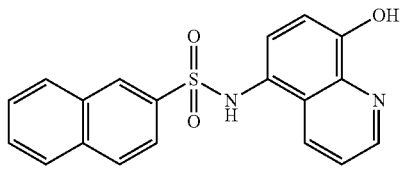

More preferably, the compound of the present invention is selected from the group consisting of compounds represented by Chemical Formulas 5, 6, 12, 17, 21, 23, and 24 above.

Disease or disorders that can be prevented or treated by the pharmaceutical composition of the present invention include various diseases related to angiogenesis. Preferably, the pharmaceutical composition of the present invention is used for prevention or treatment of uncontrolled angiogenesis-related diseases or disorders including cancers, diabetic retinopathy, retinopathy of prematurity, corneal graft rejection, neovascular glaucoma, erythema, proliferative retinopathy, psoriasis, hemophiliac joints, capillary proliferation within atherosclerotic plaques, keloids, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation, and neurodegenerative diseases.

More preferably, the disease that can be prevented or treated by the pharmaceutical composition of the present invention may be cancers, diabetic retinopathy, or proliferative retinopathy. Most preferably, the proliferative retinopathy is age-related macular degeneration.

According to another aspect of the present invention, the present invention provides a sulfonyl amide derivative selected from the group consisting of compounds represented by Chemical Formulas 2 to 4, 8, 9, 11 to 13, 15, 16 to 20, 22 to 24, 26, 28, and 29 below:

Chemical Formula 9

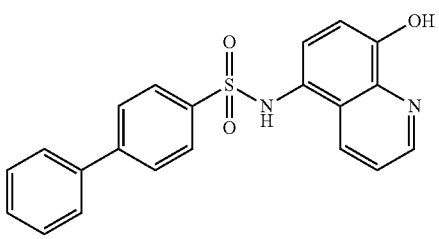

Chemical Formula 11

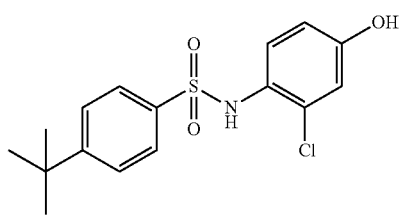

Chemical Formula 12

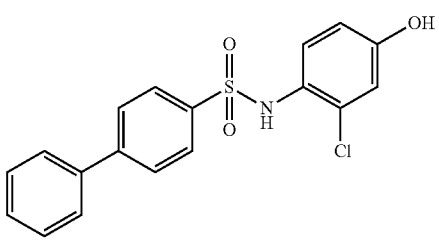

Chemical Formula 13
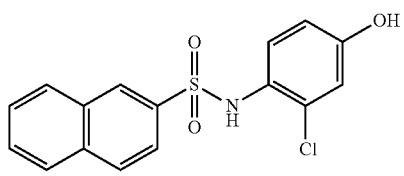

Chemical Formula 15
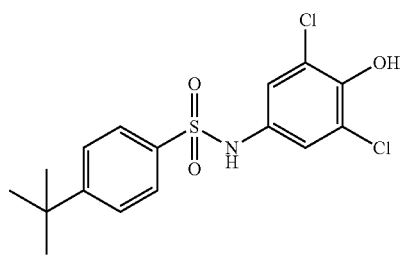

Chemical Formula 16
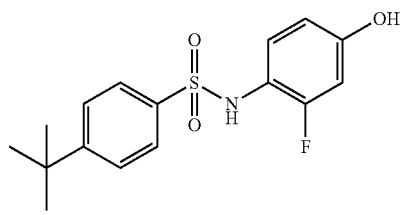

Chemical Formula 17
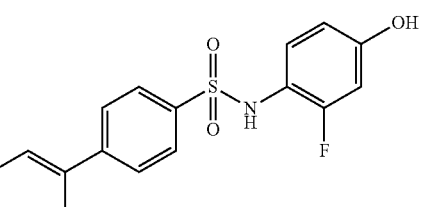

Chemical Formula 18
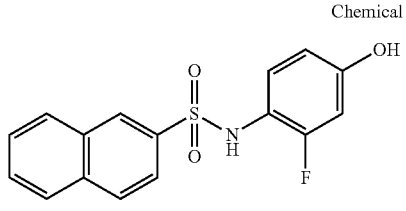

Chemical Formula 19
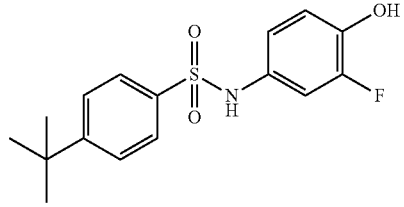

Chemical Formula 20
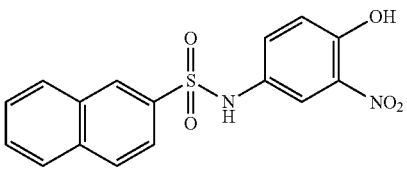

Chemical Formula 22
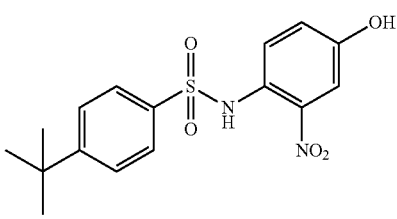

Chemical Formula 23
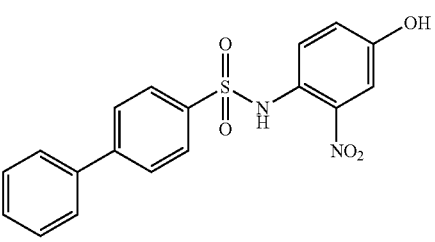

Chemical Formula 24
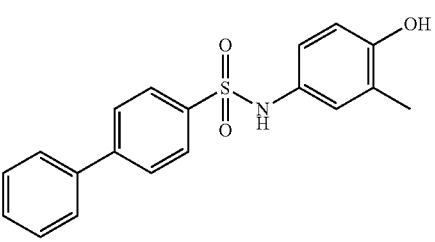

Chemical Formula 26
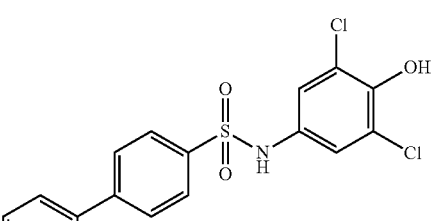

Chemical Formula 28
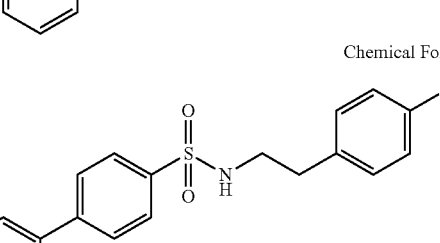

Chemical Formula 29
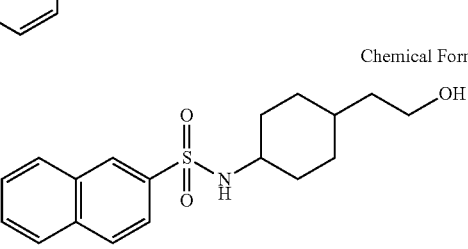

BRIEF DESCRIPTION OF THE DRAWINGS

FIG. 4 shows effects of A1893 and A1938 on in vitro angiogenesis. Serum-starved HUVECs were treated with VEGF (30 ng/mL) with or without A1893 or A1938 and then the in vitro angiogenesis analysis was performed.

DETAILED DESCRIPTION

Figure 1:
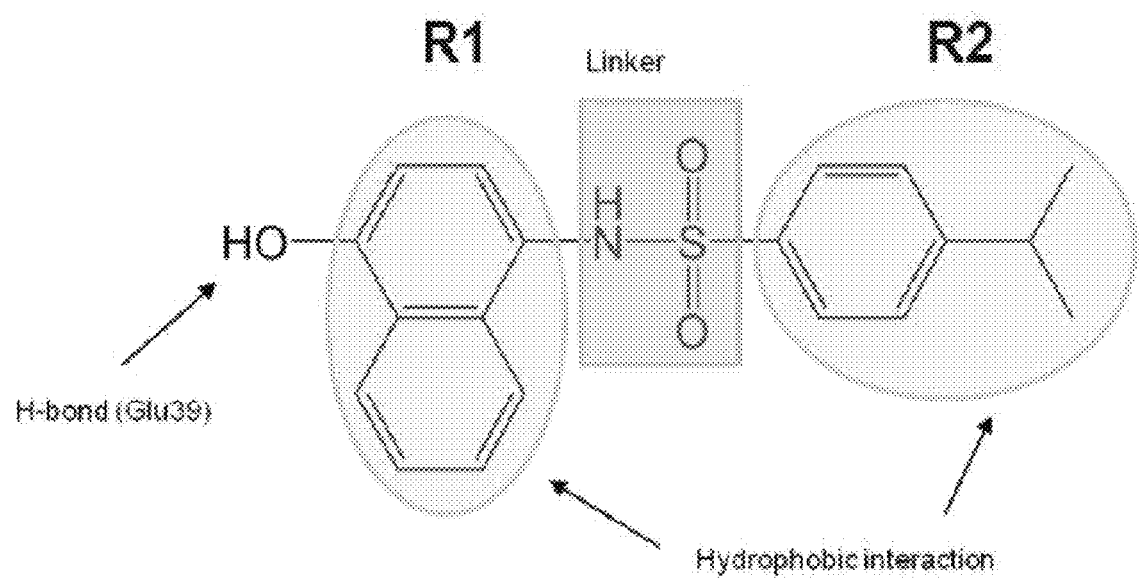
FIG. 1 shows a synthesis mechanism of a DPCN analog. DPCN is a novel low-molecular compound targeting UQCRB, and exhibits anti-angiogenic activity by modulating the oxygen-sensing function of UQCRB. The binding of DPCN and UQCRB was analyzed to synthesize DPCN derivatives having a more potent angiogenesis-inhibitory effect.
Figure 2:
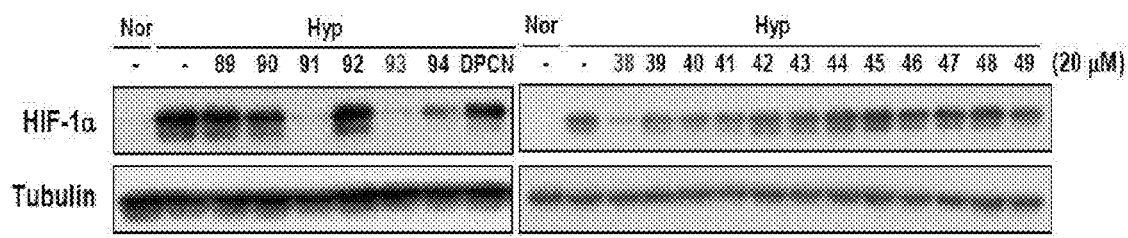
FIG. 2 shows effects of synthetic derivatives on HIF-1α accumulation. HepG2 cells were pretreated with indicated concentrations of the synthetic derivatives for 30 minutes and then exposed to 1% $O_2$ for 4 hours. HIF-1α and tubulin protein levels were analyzed using western blot analysis. When HepG2 cells were treated with A1893 and A1938, hypoxia-induced HIF-1α protein accumulation was greatly reduced.

Hereinafter, the present invention will be described in detail with reference to examples. These examples are only for illustrating the present invention more specifically, and it will be apparent to those skilled in the art that the scope of the present invention is not limited by these examples.

In accordance with an aspect of the present invention, there is provided a pharmaceutical composition for inhibiting angiogenesis, the pharmaceutical composition including, as an effective ingredient, a compound represented by Chemical Formula 1 below:

Chemical Formula 1

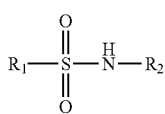

wherein, $R_1$ is

($A_1$ is straight chain or branched chain $C_1$-$C_6$ alkyl, phenyl substituted with unsubstituted or straight chain or branched chain $C_1$-$C_6$ alkyl or halogen), or naphthalyl substituted with unsubstituted or straight chain or branched chain $C_1$-$C_6$ alkyl; and $R_2$ is

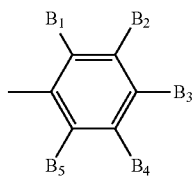

($B_1$ to $B_5$ each are independently hydrogen, halogen, hydroxy, nitro, or $C_1$-$C_6$ alkyl), hydroxy naphthalyl, 4-hydroxybenzyl $C_1$-$C_3$ alkyl, 4-(2-hydroxyethyl)cyclohexyl, or quinoline substituted with unsubstituted or straight chain or branched chain $C_1$-$C_6$ alkyl, halogen, or hydroxy.

In accordance with another aspect of the present invention, there is provided a method for prevention or treatment of uncontrolled angiogenesis-related diseases or disorders, the method including administering the pharmaceutical composition to a subject in need thereof.

The present inventors endeavored to develop an anti-angiogenesis agent for effectively inhibiting angiogenesis without cytotoxicity. As a result, the present inventors found a novel synthetic low-molecular compound targeting ubiquinol-cytochrome c reductase binding protein (UQCRB) of mitochondrial complex III, and confirmed that this compound binds to UQCRB to effectively inhibit angiogenesis.

The composition of the present invention is expressed as "a pharmaceutical composition for inhibiting angiogenesis", which may be expressed as "a pharmaceutical composition for prevention or treatment of angiogenesis-related diseases" or "a pharmaceutical composition for prevention or treatment of uncontrolled angiogenesis-related diseases".

The compound used as an effective ingredient in the pharmaceutical composition of the present invention is represented by Chemical Formula 1. The compound of the present invention basically has a sulfonyl amide backbone.

As used herein, the term "alkyl" refers to an unsubstituted saturated hydrocarbon group, and includes for example methyl, ethyl, propyl, isobutyl, pentyl, hexyl, heptyl, octyl, nonyl, decyl, undecyl, tridecyl, pentadecyl, and heptadecyl. The term straight chain or branched chain $C_1$-$C_6$ alkyl refers to a straight chain or branched chain alkyl group having an alkyl unit of 1 to 4 carbon atoms, and does not include carbon atoms of a substituent when $C_1$-$C_6$ alkyl is substituted.

As used herein, the term "hydroxybenzyl alkyl" refers to an alkyl group substituted with hydroxybenzyl (phenol). In Chemical Formula 1, the "4-hydroxybenzyl $C_1$-$C_3$ alkyl" at the $R_2$ position refers to an alkyl unit of 1 to 3 carbon atoms, which is substituted with a phenyl group substituted with a hydroxy group on the para-position.

According to a preferable embodiment of the present invention, $A_1$ of $R_1$ in Chemical Formula 1 of the present invention is methyl, ethyl, phenyl, or tert-butyl.

According to a preferable embodiment of the present invention, $B_1$ of $R_2$ in Chemical Formula 1 of the present invention is hydrogen, chloride, fluoro, hydroxy, nitro, or methyl.

According to a preferable embodiment of the present invention, hydroxy naphthalyl of $R_2$ in Chemical Formula 1 of the present invention is 7-hydroxy naphthalyl.

According to a preferable embodiment of the present invention, quinoline of $R_2$ in Chemical Formula 1 of the present invention is 8-hydroxy quinoline.

According to a preferable embodiment of the present invention, the compound of the present invention is selected from the group consisting of compounds represented by Chemical Formulas 2 to 29 below.

Chemical Formula 2

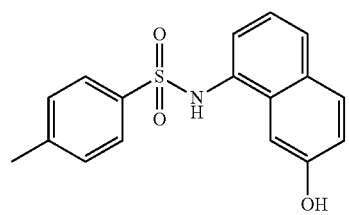

Chemical Formula 3

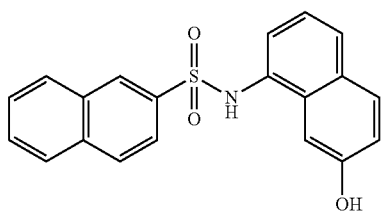

Chemical Formula 4

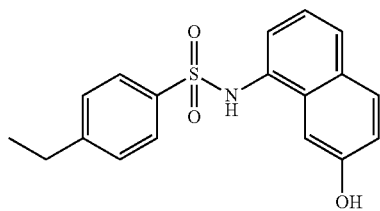

Chemical Formula 5

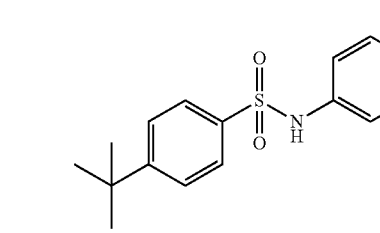

Chemical Formula 6

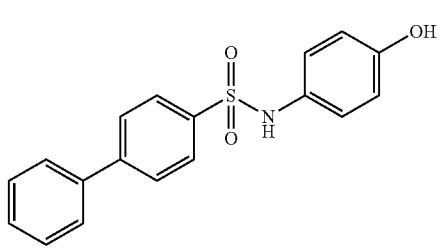

Chemical Formula 7

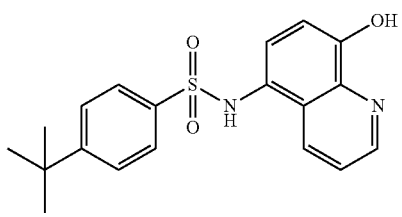

Chemical Formula 8

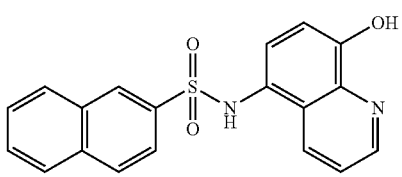

Chemical Formula 9

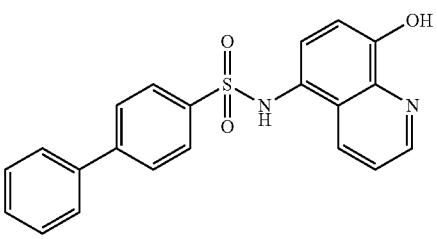

Chemical Formula 10

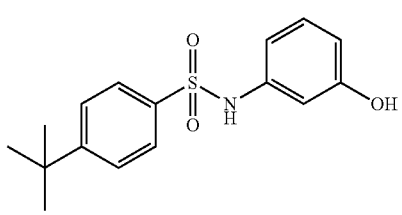

Chemical Formula 11

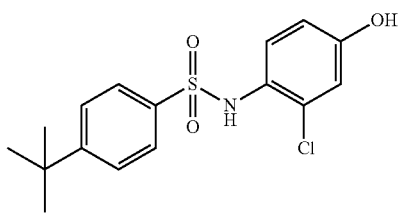

Chemical Formula 12

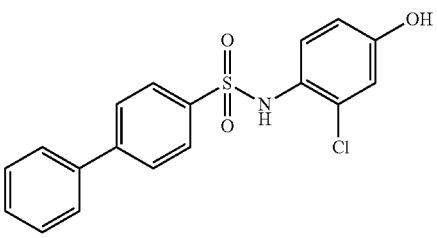

Chemical Formula 13

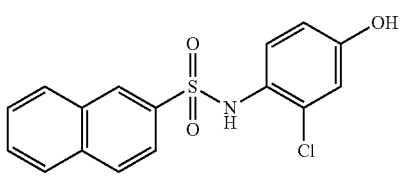

Chemical Formula 14
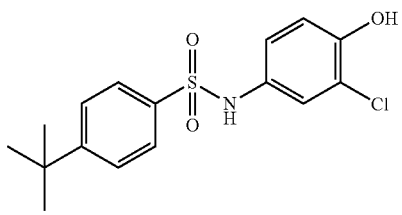
Chemical Formula 15
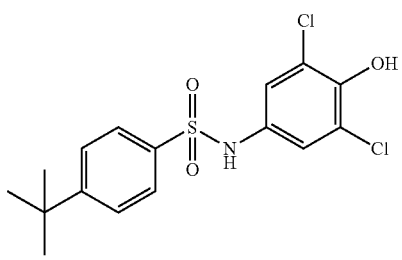
Chemical Formula 16
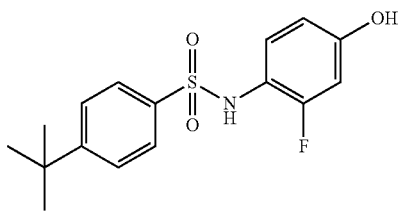
Chemical Formula 17
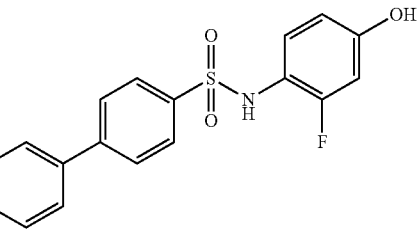
Chemical Formula 18
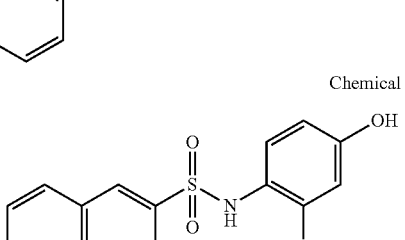
Chemical Formula 19
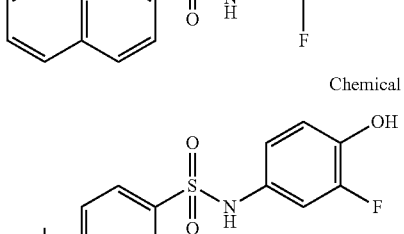
Chemical Formula 20
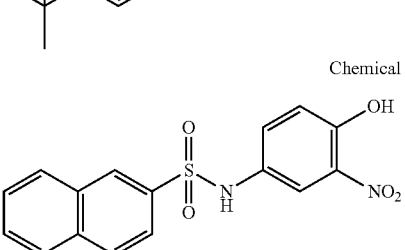
Chemical Formula 21
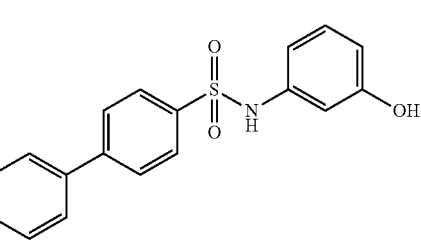
Chemical Formula 22
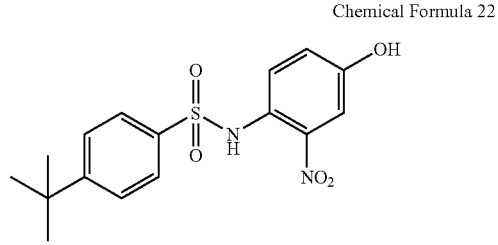
Chemical Formula 23
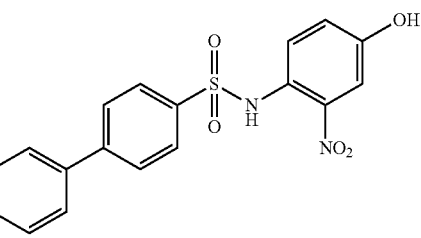
Chemical Formula 24
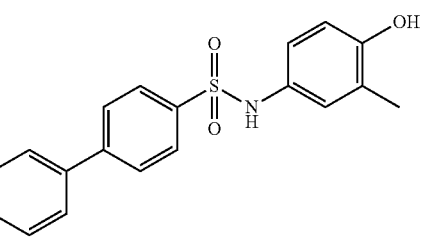
Chemical Formula 25
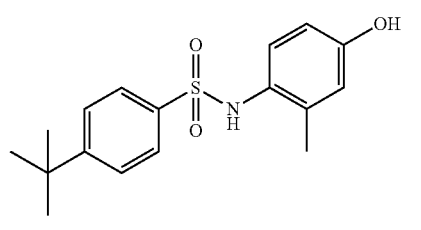
Chemical Formula 26
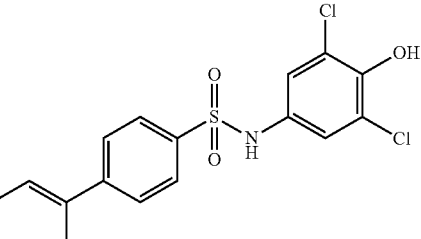

Chemical Formula 27

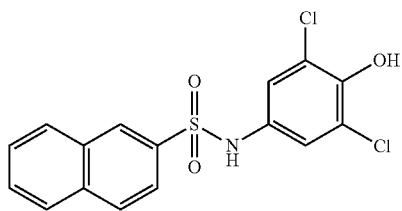

Chemical Formula 28

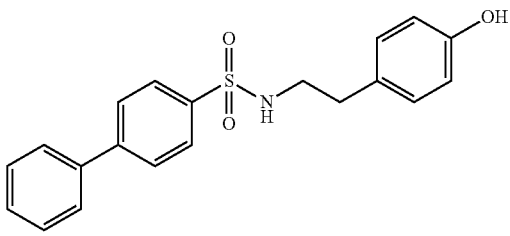

Chemical Formula 29

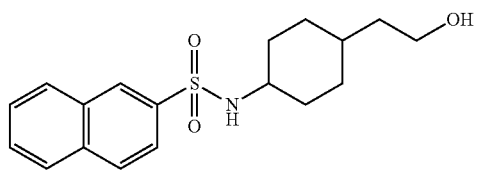

More preferably, the compound of the present invention is selected from the group consisting of compounds represented by Chemical Formulas 5, 6, 12, 17, 21, 23, and 24 above.

According to the present invention, the seven compounds listed above have low $IC_{50}$ values in the view of the HIF-1α protein level. Therefore, these may be used as effective compositions for treatment of various diseases related to angiogenesis.

Disease or disorders that can be prevented or treated by the pharmaceutical composition of the present invention include various diseases related to angiogenesis. Preferably, the pharmaceutical composition of the present invention is used for prevention or treatment of uncontrolled angiogenesis-related diseases or disorders including cancers, diabetic retinopathy, retinopathy of prematurity, corneal graft rejection, neovascular glaucoma, erythema, proliferative retinopathy, psoriasis, hemophiliac joints, capillary proliferation within atherosclerotic plaques, keloids, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation, and neurodegenerative diseases.

Examples of the autoimmune diseases that can be prevented or treated by the composition of the present invention may include, but are not limited to, alopecia greata, ankylosing spondylitis, antiphospholipid syndrome, autoimmune Addison's disease, autoimmune adrenal disease, autoimmune hemolytic anemia, autoimmune hepatitis, autoimmune ovaritis and testitis, autoimmune thrombocytopenia, Behcet's disease, bullous pemphigoid, cardiomyopathy, celiac sprue-dermatitis, chronic fatigue immune dysfunction syndrome, chronic inflammatory demyelinating polyradiculoneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Grave's disease, Guillain-Barre syndrome, Hashimoto's thyroiditis, idiopathic pulmonary fibrosis, idiopathic thrombocytopenic purpuras, IgA nephropathy, juvenile arthritis, lichen planus, lupus erythematosus, Meniere's disease, mixed connective tissue disease, multiple sclerosis, type I or immune-mediated diabetes, myasthenia gravis, pemphigus vulgaris, pernicious anemia, polyarteritis nodosa, polychondritis, autoimmune polyglandular syndrome, polymyalgia rheumatica, polymyositis and dermatomyositis, primary agammaglobulinemia, primary biliary cirrhosis, psoriasis, psoriatic arthritis, Raynaud's phenomenon, Reiter's syndrome, rheumatoid arthritis, Sarcoidosis, scleroderma, stiff-person syndrome, systemic lupus erythematosus, lupus erythematosus, Takayasu's arteritis, temporal arteritis, giant cell arteritis, ulcerative colitis, uveitis, vitiligo and Wegener's granulomatosis.

Examples of the inflammatory diseases that can be prevented or treated by the composition of the present invention may include, but are not limited to, asthma, encephilitis, inflammatory enteritis, chronic obstructive pulmonary disease, allergy, septic shock, pulmonary fibrosis, undifferentiated spondyloarthropathy, undifferentiated arthropathy, arthritis, inflammatory osteolysis, and chronic inflammation by chronic viral or bacterial infections.

More preferably, the disease that can be prevented or treated by the pharmaceutical composition of the present invention may be cancers, diabetic retinopathy, or proliferative retinopathy. Most preferably, the proliferative retinopathy is age-related macular degeneration.

Preferably, the pharmaceutical composition of the present invention may include a pharmaceutically acceptable carrier. The pharmaceutically acceptable carriers included in the pharmaceutical composition of the present invention are conventionally used in formulations, and examples thereof include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include, besides the above components, a lubricant, a wetting agent, a sweetening agent, a flavoring agent, an emulsifier, a suspending agent, a preservative, and the like. Appropriate pharmaceutically acceptable carriers and agents are described in detail in *Remington's Pharmaceutical Sciences* (19th ed., 1995).

The pharmaceutical composition of the present invention may be administered orally or parenterally. Examples of parenteral administration may include intravenous, subcutaneous, intramuscular, intraperitoneal, and transdermal injections.

The appropriate dose of the pharmaceutical composition of the present invention may be varied depending on factors, such as formulating method, manner of administration, age, body weight, sex, and morbidity of patient, food, time of administration, route of administration, excretion rate, and response sensitivity. The dose per day of the pharmaceutical composition of the present invention may be, for example, 0.001 to 100 mg/kg.

The pharmaceutical composition of the present invention may be formulated into a unit dosage form or injected in a multidose container by using a pharmaceutically acceptable carrier and/or excipient, according to the method easily conducted by a person having ordinary skills in the art to which the present invention pertains. Here, the dosage form may be a solution in an oily or aqueous medium, a suspension, a syrup, or an emulsion, an extract, a powder, a granule, a tablet, or a capsule, and may further include a dispersant or a stabilizer.

According to another aspect of the present invention, the present invention provides a sulfonyl amide derivative selected from the group consisting of compounds represented by Chemical Formulas 2 to 4, 8, 9, 11 to 13, 15, 16 to 20, 22 to 24, 26, 28, and 29 below:

Chemical Formula 2
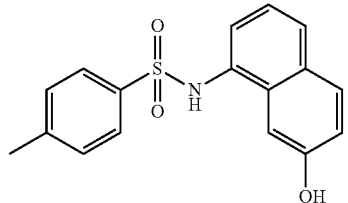

Chemical Formula 3
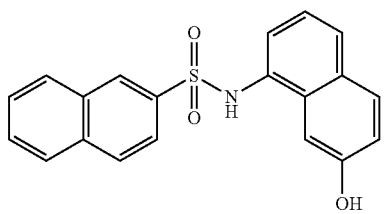

Chemical Formula 4
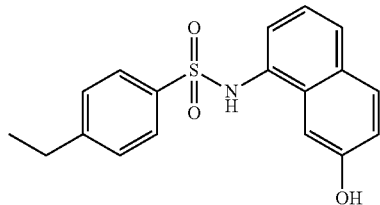

Chemical Formula 8
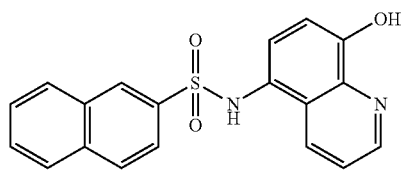

Chemical Formula 9
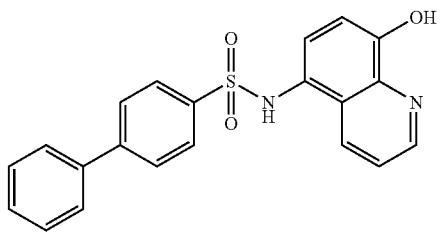

Chemical Formula 11
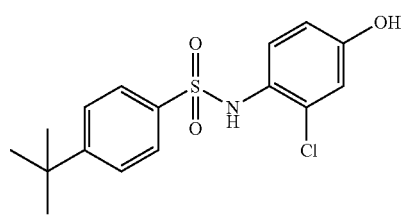

-continued

Chemical Formula 12
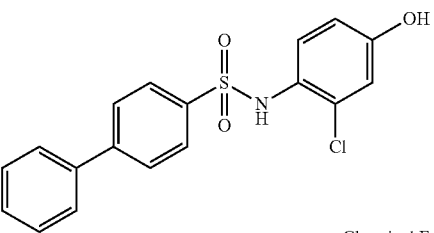

Chemical Formula 13
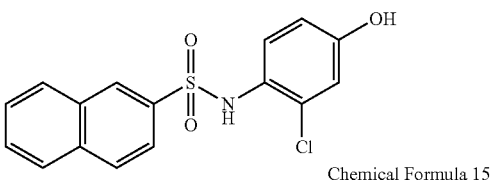

Chemical Formula 15
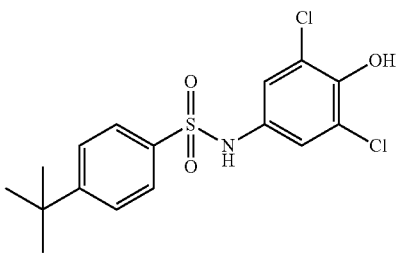

Chemical Formula 16
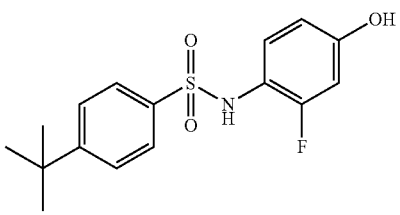

Chemical Formula 17
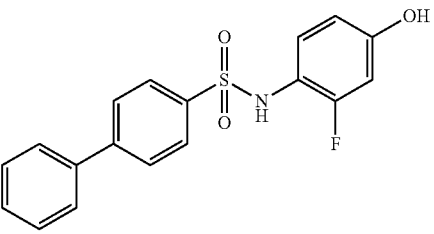

Chemical Formula 18
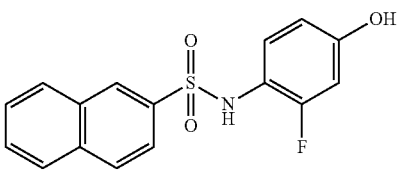

Chemical Formula 19
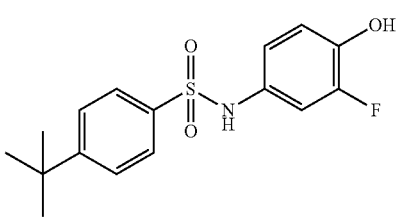

Chemical Formula 20

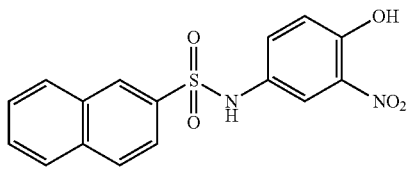

Chemical Formula 22

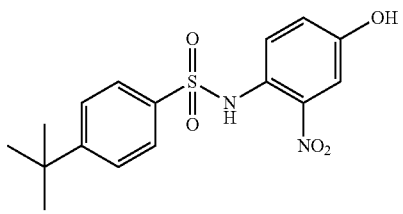

Chemical Formula 23

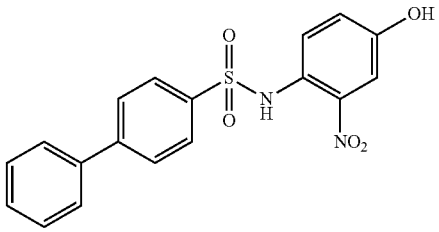

Chemical Formula 24

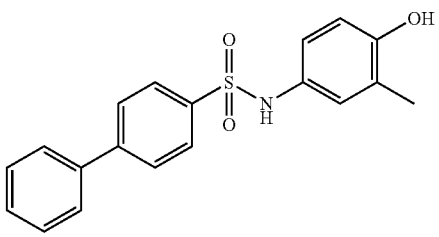

Chemical Formula 26

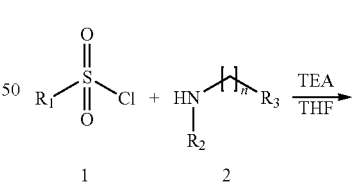

Chemical Formula 28

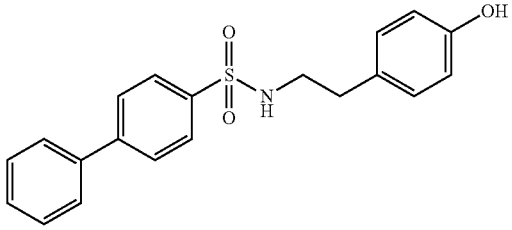

Chemical Formula 29

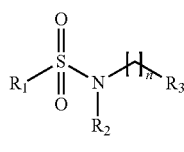

Features and advantages of the present invention are summarized as follows:

(a) The present invention provides a pharmaceutical composition for inhibiting angiogenesis and a novel sulfonyl amide derivative compound, which can be effectively used for prevention or treatment of angiogenesis-related diseases or disorders.

(b) The compound used as an effective ingredient in the pharmaceutical composition of the present invention specifically binds to UQCRB to inhibit biological functions thereof, thereby inhibiting angiogenic responses without inducing apoptosis, leading to a great improvement in the safety of drugs.

EXAMPLES

Preparation of Compounds

In the synthesis mechanism below, Reactant 2 (an amine derivative) was added to Reactant 1 (a sulfonyl chloride derivative) in a 0.1 M solution of tetrahydrofuran, followed by stirring at room temperature, and then triethyl amine was added thereto, followed by stirring at room temperature for 12 hours. After that, the mixture was filtered with ethyl acetate, and then concentrated under reduced pressure. The thus obtained compound was subjected to silica gel column chromatography or recrystallization, thereby obtaining Product 3.

Synthesis Mechanism

Preparation of the compounds of the present invention based on the synthesis mechanism above will be described by taking A2060 (preparation of biphenyl-4-sulfonic acid [2-(4-hydroxy-phenyl)-ethyl]-amide) as an example, as follows.

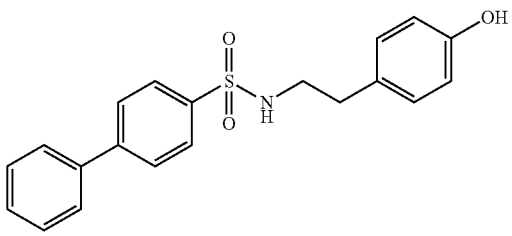 [SMILES: O=S(=O)(NCCc1ccc(O)cc1)c1ccc(-c2ccccc2)cc1]

While biphenyl-4-sulfonyl chloride (1, 300 mg, 1.19 mmol) and 0.1 M tertrahydrofuran were stirred, 4-(2-aminoethyl)phenol (2, 217 mg, 1.25 mmol) and triethyl amine (497 ml, 3.57 mmol) were introduced thereinto, followed by stirring at room temperature for 12 hours. The resultant mixture was filtered with ethyl acetate, and then concentrated under reduced pressure. The thus obtained mixture was subjected to purification through a silica gel column chromatography (eluent-hexane:ethylacetate=1:5) or recrystallization with ethyl alcohol. The target compound was obtained at a yield of 250 (104 mg, 0.29 mmol).

500 MHz, DMSO-d6, δ 9.18 (s, 1H), 7.86 (q, 4H, J=9.0 Hz), 7.74 (d, 3H, J=8.5 Hz), 7.51 (t, 2H, J=7.5 Hz), 7.44 (t, 1H, J=7.5 Hz), 6.94 (d, 2H, J=8.5 Hz), 6.64 (d, 2H, J=8.5 Hz), 2.92 (t, 2H, J=9.3 Hz), 2.58 (t, 2H, J=7.5 Hz) ESI (m/z) 354.10 (M+), 376.10 (MNa+)

The other compounds of the present invention were prepared by the same method as in the foregoing synthesis mechanism and the representative preparative example, and their spectroscopic data were tabulated in Table 1.

TABLE 1

| KBH-A-Nr | IUPAC name | LC/MS | 1H NMR |
|---|---|---|---|
| A1882 | N-(7-hydroxy-naphthalen-1-yl)-4-methyl-benzene-sulfonamide | ESI (m/z) 314.00 (M+), 355.00 (MAc+) | 500 MHz, DMSO-d6, δ 7.86 (d, 1H, J = 2.5 Hz), 7.75 (d, 2H, J = 8.5 Hz), 7.69 (d, 2H, J = 9.0 Hz), 7.46 (d, 2H, J = 8.0 Hz), 7.22 (t, 1H, J = 7.7 Hz), 7.06 (d, 1H, J = 8.0 Hz), 6.93 (dd, 1H, J = 2.5, 9.0 Hz), 6.69 (d, 1H, J = 7.5 Hz), 5.76 (s, 2H), 2.41 (s, 3H) |
| A1883 | naphthalene-2-sulfonic acid (7-hydroxy-naphthalen-1-yl)-amide | ESI (m/z) 350.00 (M+), 391.00 (MAc+) | 500 MHz, DMSO-d6, δ 8.59 (s, 1H), 8.21 (d, 2H, J = 9.0 Hz), 8.11 (d, 1H, J = 8.0 Hz), 7.92-7.89 (m, 2H), 7.78 (t, 1H, J = 7.2 Hz), 7.70 (t, 1H, J = 7.2 Hz), 7.65 (t, 1H, J = 8.5 Hz), 7.20 (t, 1H, J = 7.7 Hz), 7.03 (d, 1H, J = 8.0 Hz), 6.92 (dd, 1H, J = 2.3, 8.8 Hz), 6.67 (d, 1H, J = 7.5 Hz), 5.74 (s, 2H) |
| A1891 | 4-ethyl-N-(7-hydroxy-naphthalen-1-yl)-benzene-sulfonamide | ESI (m/z) 328.00 (M+), 369.00 (MAc+) | 500 MHz, DMSO-d6, δ 7.87 (d, 1H, J = 2.5 Hz), 7.80-7.78 (m, 2H), 7.70 (d, 1H, J = 9.0 Hz), 7.49 (d, 2H, J = 8.5 Hz), 7.22 (t, 1H, J = 7.8 Hz), 7.07 (d, 1H, J = 8.0 Hz), 6.95 (dd, 1H, J = 2.0, 9.0 Hz), 6.70 (d, 1H, J = 7.5 Hz), 2.76 (s, 2H), 2.70 (q, 2H, J = 7.5 Hz), 1.19 (t, 3H, J = 7.7 Hz) |
| A1893 | 4-tert-butyl-N-(4-hydroxy-phenyl)-benzene-sulfonamide | ESI (m/z) 347.00 (MAc+) | 500 MHz, DMSO-d6, δ 9.73 (s, 1H), 9.28 (s, 1H), 7.59 (d, 2H, J = 8.5 Hz), 7.54 (d, 2H, J = 9.0 Hz), 6.86 (d, 2H, J = 9.0 Hz), 6.59 (d, 2H, J = 9.0 Hz), 1.26(s, 9H) |
| A1938 | biphenyl-4-sulfonic acid (4-hydroxy-phenyl)-amide | APCI (m/z) 326.00 (M+) | 500 MHz, DMSO-d6, δ 9.80 (s, 1H), 9.32 (s, 1H), 7.83 (d, 8.4 Hz, 2H), 7.72 (t, J = 7.9 Hz, 4H), 7.49 (t, J = 7.6 Hz, 2H), 7.42 (t, J = 7.3 Hz, 1H), 6.88 (d, J = 8.8 Hz, 2H), 6.61 (d, J = 8.8 Hz, 2H). |
| A1958 | 4-tert-butyl-N-(8-hydroxy-quinolin-5-yl)-benzene-sulfonamide | ESI (m/z) 357.00 (M+) | 500 MHz, DMSO-d6, δ 10.28 (s, 1H), 8.99 (d, J = 4.0 Hz, 1H), 8.71 (d, J = 8.4 Hz, 1H), 7.80 (dd, J = 8.4, 4.9 Hz, 1H), 7.50 (s, 4H), 7.31 (d, J = 8.3 Hz, 1H), 7.17 (d, J = 8.4 Hz, 1H), 1.25 (s, 9H). |
| A1959 | naphthalene 2-sufonic acid (8-hydroxy-quinolin-5-yl)-amide | ESI (m/z) 351.00 (M+) | 500 MHz, DMSO-d6, δ 10.37 (s, 1H), 8.96 (d, 1H, J = 5.0 Hz), 8.85 (d, 1H, J = 7.0 Hz), 8.20 (s, 1H), 8.11 (d, 2H, J = 9.0 Hz), 8.04 (t, 2H, J = 7.8 Hz), 7.76 (dd, 1H, J = 1.7, 8.8 Hz), 7.70 (t, 2H, J = 8.0 Hz), 7.62 (t, 1H, J = 7.5 Hz), 7.15 (d, 1H, J = 8.5 Hz), 7.02 (d, 1H, J = 8.0 Hz) |
| A1961 | biphenyl-4-sulfonic acid (8-hydroxy-quinolin-5-yl)-amide | ESI (m/z) 376.95 (M+) | 500 MHz, DMSO-d6, δ 10.23 (s, 1H), 8.94 (d, 1H, J = 4.0 Hz), 7.82 (d, 2H, J = 9.0 Hz), 7.77-7.67 (m, 4H), 7.50 (t, 3H, J = 8.0 Hz), 7.47-7.42 (m, 3H), 7.16 (d, 1H, J = 8.0 Hz), 7.11 (d, 1H, J = 8.0 Hz) |
| A1999 | 4-tert-butyl-N-(3-hydroxy-phenyl)-benzene-sulfonamide | ESI (m/z) 306.05 (M+) | 500 MHz, DMSO-d6, δ 10.16 (s, 1H), 9.43 (s, 1H), 7.70 (d, 1H, J = 8.3 Hz), 7.57 (d, 2H, J = 8.0 Hz), 6.97 (t, 1H, J = 8.0 Hz), 6.60 (s, 1H), 6.53 (d, 1H, J = 8.0 Hz), 6.38 (d, 1H, J = 8.0 Hz), 1.26 (s, 9H) |
| A2000 | 4-tert-butyl-N-(2-chloro-4-hydroxy-phenyl)-benzene-sulfonamide | ESI (m/z) 340.05 (M+_1), 342.05 (M++1), 381.05 (MAc+_1), 383.05 (MAc++1) | 500 MHz, DMSO-d6, δ 7.71 (q, 4H, J = 9.0 Hz), 6.77 (t, 1H, J = 1.2 Hz), 6.68 (d, 2H, J = 1.5 Hz), 5.51 (s, 2H), 1.30 (s, 9H) |
| A2001 | biphenyl-4-sulfonic acid (2-chloro-4-hydroxy-phenyl)-amide | ESI (m/z) 360.00 (M+), 401.00 (MAc+) | 500 MHz, DMSO-d6, δ 7.97 (d, 2H, J = 8.5 Hz), 7.89 (d, 2H, J = 8.5 Hz), 7.78 (d, 2H, J = 7.5 Hz), 7.53 (t, 2H, J = 7.5 Hz), 7.47 (q, 1H, J = 7.0 Hz), 6.56 (d, 1H, J = 2.0 Hz), 6.72-6.68 (m, 2H), |
| A2002 | naphthalene-2-sulfonic acid (2-chloro-4-hydroxy-phenyl)-amide | ESI (m/z) 334.05 (M+_1), 336.05 (M++1), 374.95 (MAc+_1), 376.95 (MAc++1) | 500 MHz, DMSO-d6, δ 8.54 (s, 1H), 8.23-8.21 (m, 2H), 8.12 (d, 1H, J = 8.0 Hz), 7.83 (dd, 1H, J = 2.0, 8.5 Hz), 7.79 (t, 1H, J = 7.5 Hz), 7.71 (tm, 1H, J-7.5 Hz), 6.91 (s, 1H), 6.62 (s, 2H), 5.49 (s, 2H) |
| A2003 | 4-tert-butyl-N-(3-chloro-4-hydroxy-phenyl)-benznene-sulfonamide | ESI (m/z) 340.05 (M+_1), 342.05 (M++1), 381.05 (MAc+_1), 383.05 (MAc++1) | 500 MHz, DMSO-d6, δ 7.76 (d, 2H, J = 9.0 Hz), 7.68 (d, 2H, J = 8.5 Hz), 6.93 (d, 1H, J = 9.0 Hz), 6.56 (d, 1H, J = 2.5 Hz), 6.45 (dd, 1H, J = 2.5, 9.0 Hz), 5.53 (s, 2H), 1.26 (s, 9H) |
| A2006 | 4-tert-butyl-N-(3,5- | ESI (m/z) 373.95 | 500 MHz, DMSO-d6, δ 7.87 (d, 2H, J = 8.5 Hz), 7.71 (d, 2H, J = 8.5 Hz), 6.60 (s, 2H), 5.82 (s, 2H), |

TABLE 1-continued

Spectroscopic data of respective compounds

| KBH-A-Nr | IUPAC name | LC/MS | 1H NMR |
|---|---|---|---|
| | dichloro-4-hydroxy-phenyl)-benzene-sulfonamide | (M+_1), 375.95 (M++1), 415.00 (MAc+_1), 417.05 (MAc++1) | 1.32 (s, 9H) |
| A2007 | 4-tert-butyl-N-(2-fluoro-4-hydroxy-phenyl)-benzene-sulfonamide | ESI (m/z) 324.00 (M+), 365.05 (MAc+) | 500 MHz, DMSO-d6, δ 7.74 (d, 2H, J = 9.0 Hz), 7.67 (d, 2H, J = 8.5 Hz), 6.69 (dd, 1H, J = 2.5, 11.5 Hz), 6.94 (t, 1H, J = 9.5 Hz), 6.53 (dd, 1H, J = 2.5, 9.0 Hz), 5.29 (s, 2H), 1.26 (s, 9H) |
| A2008 | biphenyl-4-sulfonic acid (2-fluoro-4-hydroxy-phenyl)-amide | ESI (m/z) 344.00 (M+), 385.05 (MAc+) | 500 MHz, DMSO-d6, δ 7.96 (d, 2H, J = 8.5 Hz), 7.87 (d, 2H, J = 8.5 Hz), 7.78 (d, 2H, J = 7.0 Hz), 7.53 (t, 2H, J = 7.1 Hz), 7.47 (t, 1H, J = 7.2 Hz), 6.78 (dd, 1H, J = 2.5, 11.5.0 Hz), 6.64 (t, 1H, J = 8.5 Hz), 6.57 (d, 1H, J = 9.0 Hz), 5.31 (s, 2H) |
| A2009 | naphthalene-2-sulfonic acid (2-fluoro-4-hydroxy-phenyl)-amide | ESI (m/z) 318.00 (M+), 359.05 (MAc+) | 500 MHz, DMSO-d6, δ 8.53 (s, 1H), 8.22-8.20 (m, 2H), 8.11 (d, 2H, J = 8.5 Hz), 7.83 (d, 2H, J = 7.5 Hz), 7.79 (t, 1H, J = 7.5 Hz), 7.71 (t, 1H, J = 7.5 Hz), 6.76 (dd, 1H, J = 2.3, 11.8 Hz), 6.59 (t, 1H, J = 9.5 Hz), 6.50 (t, 1H, J = 9.0 Hz), 5.27 (s, 2H) |
| A2010 | 4-tert-butyl-N-(3-fluoro-4-hydroxy-phenyl)-benzene-sulfonamide | ESI (m/z) 324.00 (M+), 346.00 (MNa+) | 500 MHz, DMSO-d6, δ 7.75 (d, 2H, J = 8.5 Hz), 7.69 (d, 2H, J = 8.5 Hz), 6.71 (t, 1H, J = 9.5 Hz), 6.52 (dd, 1H, J = 2.5, 13.0 Hz), 6.26 (dd, 1H, J = 2.5, 9.0 Hz), 5.54 (s, 2H), 1.31 (s, 9H) |
| A2013 | Naphthalene-2-sulfonic acid (3-nitro-4-hydroxy-phenyl)-amide | ESI (m/z) 345.00 (M+), 367.05 (MNa+) | 500 MHz, DMSO-d6, δ 8.51 (s, 1H), 8.23-8.21 (m, 2H), 8.12 (d, 1H, J = 8.0 Hz), 7.82-7.76 (m, 2H), 7.72 (t, 1H, J = 7.5 Hz), 7.05 (d, 1H, J = 2.5 Hz), 6.73 (d, 1H, J = 9.0 Hz), 6.68 (dd, 1H, J = 2.5, 9.0 Hz), 5.92 (s, 1H), 3.36 (s, 1H) |
| A2033 | biphenyl-4-sulfonic acid (3-hydroxy-phenyl)-amide | | 500 MHz, DMSO-d6, δ 7.95 (q, 4H, J = 24.5 Hz), 7.77 (d, 2H, J = 7.0 Hz), 7.67 (d, 1H, J = 8.5 Hz), 7.61 (d, 1H, J = 8.0 Hz), 7.53 (t, 3H, J = 8.3 Hz), 7.48 (t, 2H, J = 7.2 Hz), 7.17 (dd, 1H, J = 2.8, 9.2 Hz), 6.98 (d, 1H, J = 9.5 Hz) |
| A2037 | 4-tert-butyl-N-(2-nitro-4-hydroxy-phenyl)-benzene-sulfonamide | ESI (m/z) 351.00 (M+), 373.05 (MNa+) | 500 MHz, DMSO-d6, δ 7.78 (d, 2H, J = 8.5 Hz), 7.69 (d, 2H, J = 8.5 Hz), 7.55 (s, 2H), 7.32 (d, 1H, J = 3.0 Hz), 7.16 (dd, 1H, J = 2.8, 9.0 Hz), 6.98 (d, 1H, J = 9.0 Hz), 1.30 (s, 9H) |
| A2038 | biphenyl-4-sulfonic acid (2-nitro-4-hydroxy-phenyl)-benzene-sulfonamide | ESI (m/z) 371.00 (M+), 393.00 (MNa+) | 500 MHz, DMSO-d6, δ 7.94 (q, q, 4H, J = 25.3 Hz), 7.78 (d, 2H, J = 7.5 Hz), 7.53 (t, 2H, J = 7.5 Hz), 7.47 (t, 1H, J = 7.5 Hz), 6.95 (t, 1H, J = 8.0 Hz), 6.45 (d, 1H, J = 9.0 Hz), 6.30 (s, 1H), 6.08 (d, 1H, J = 5.5 Hz), 5.40 (s, 2H) |
| A2040 | biphenyl-4-sulfonic acid (4-hydroxy-3-methyl-phenyl)-amide | ESI (m/z) 340.05 (M+), 381.10 (MAc+) | 500 MHz, DMSO-d6, δ 9.73 (s, 1H), 9.19 (s, 1H), 7.83 (d, 2H, J = 8.5 Hz), 7.74-7.70 (m, 4H), 7.49 (t, 2H, J = 7.2 Hz), 7.42 (t, 1H, J = 6.8 Hz), 6.79 (s, 1H), 6.70 (d, 1H, J = 8.5 Hz), 6.60 (d, 1H, J = 8.5 Hz), 1.9 (s, 3H) |
| A2041 | biphenyl-4-sulfonic acid (4-hydrox-3-methyl-phenyl)-amide | ESI (m/z) 340.05 (M+), 381.10 (MAc+) | 500 MHz, DMSO-d6, δ 7.97 (d, 2H, J = 8.5 Hz), 7.92 (d, 2H, J = 8.5 Hz), 7.77 (d, 2H, J = 7.5 Hz), 7.68-7.66 (m, 3H), 7.61 (d, 2H, J = 8.0 Hz), 7.66 (t, 2H, J = 7.6 Hz), 7.37 (t, 1H, J = 7.6 Hz). 2.17 (s, 3H) |
| A2043 | biphenyl-4-sulfonic acid (3,5-dichloro-4-hydroxy-phenyl)-amide | ESI (m/z) 393.95 (M+_1), 395.90 (M++1), 415.90 (MAc+_1), 417.95 (MAc++1) | 500 MHz, DMSO-d6, δ 8.01 (q, 4H, J = 8.5 Hz), 7.79 (d, 2H, J = 7.0 Hz), 7.54 (t, 2H, J = 7.5 Hz), 7.48 (t, 1H, J = 7.0 Hz), 6.63 (s, 2H), 5.84 (s, 2H) |
| A2044 | naphthalene-3-sulfonic acid (3,5-dichloro-4-hydroxy-phenyl)-amide | ESI (m/z) 367.95 (M+_1), 369.95 (M++1), 389.80 (MNa+_1), 391.90 (MNa++1) | 500 MHz, DMSO-d6, δ 8.67 (s, 1H), 8.27 (d, 1H, J = 8.5 Hz), 8.22 (d, 1H, J = 8.5 Hz), 8.12 (d, 1H, J = 8.5 Hz), 7.95 (d, 1H, J = 8.5 Hz), 7.79 (t, 1H, J = 7.5 Hz), 7.72 (t, 1H, J = 7.5 Hz), 6.59 (s, 2H), 5.83 (s, 2H) |
| A2060 | biphenyl-4-sulfonic acid [2-(4-hydroxy-phenyl)-ethyl]-amide | ESI (m/z) 354.10 (M+), 376.10 (MNa+) | 500 MHz, DMSO-d6, δ 9.18 (s, 1H), 7.86 (q, 4H, J = 9.0 Hz), 7.74 (d, 3H, J = 8.5 Hz), 7.51 (t, 2H, J = 7.5 Hz), 7.44 (t, 1H, J = 7.5 Hz), 6.94 (d, 2H, J = 8.5 Hz), 6.64 (d, 2H, J = 8.5 Hz), 2.92 (t, 2H, J = 9.3 Hz), 2.58 (t, 2H, J = 7.5 Hz) |
| A2069 | naphthalene-2-sulfonic acid [4-(2-hydroxy-ethyl)-cyclohenxyl]-amide | ESI (m/z) 334.15 (M+), 356.10 (MNa+) | 500 MHz, DMSO-d6, δ 8.43 (s, 1H), 8.15 (d, 1H, J = 8.0 Hz), 8.12 (d, 1H, J = 9.0 Hz), 8.03 (d, 1H, J = 8.0 Hz), 7.88-7.82 (m, 1H), 7.71-7.65 (m, 3H), 4.27-4.23 (m, 1H), 3.18 (s, 1H), 3.38-3.30 (m, 2H), 1.57 (t, 2H, J = 13.2 Hz), 1.40-1.30 (m, 6H), 1.21-1.18 (m, 1H), 1.20 (d, 1H, J = 12.0 Hz), 0.81 (q, 1H, J = 11.0 Hz) |

HIF-1α Stability Analysis

HepG2 cells were pretreated with indicated concentrations of the synthetic derivatives for 30 minutes and then exposed to 1% $O_2$ for 4 hours. HIF-1α and tubulin protein levels were analyzed using western blot analysis. When HepG2 cells were treated with A1893 and A1938, hypoxia-induced HIF-1α protein accumulation was greatly reduced (Table 2 and FIG. 1).

TABLE 2

$IC_{50}$ values of respective compounds on HIF-1 α

| KBH-A-Nr | $IC_{50}$ (μM) |
|---|---|
| A1882 | 20 |
| A1883 | 20 |
| A1891 | 10 |
| A1893 | 5 |
| A1938 | 5 |
| A1958 | 20 |
| A1959 | 20 |
| A1961 | 20 |
| A1999 | 20 |
| A2000 | 10 |

TABLE 2-continued

IC$_{50}$ values of respective compounds on HIF-1 α

| KBH-A-Nr | IC$_{50}$ (μM) |
|---|---|
| A2001 | 5 |
| A2002 | 20 |
| A2003 | 10 |
| A2006 | 10 |
| A2007 | 10 |
| A2008 | 5 |
| A2009 | 20 |
| A2010 | 10 |
| A2013 | 20 |
| A2033 | 5 |
| A2037 | 10 |
| A2038 | 5 |
| A2040 | 5 |
| A2041 | 10 |
| A2043 | 10 |
| A2044 | 10 |
| A2060 | 10 |
| A2069 | 10 |

Hereinafter, additional experiments were conducted using two compounds having the lowest IC$_{50}$ value, A1893 and A1938.

Surface Plasmon Resonance (SPR) Analysis

Figure 3:
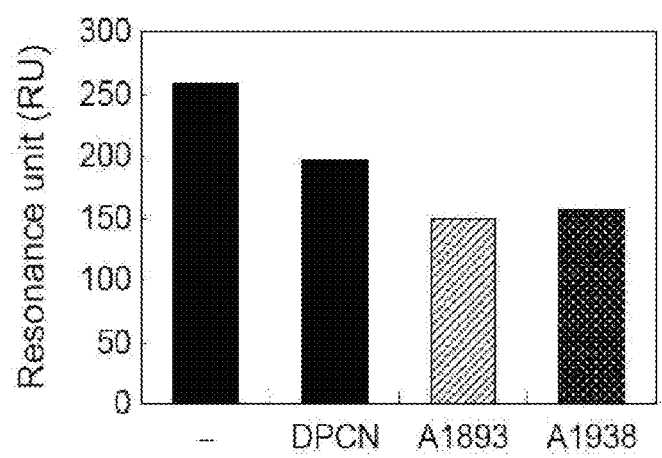
FIG. 3 shows analysis results of the interaction between selected compounds and UQCRB. SPR analysis was performed to analyze the binding of the compounds to UQCRB. Control biotin and biotinylated terpestacin (BT) were sequentially immobilized onto the surface of a streptavidin-coated sensor chip and the apparent binding affinities were calculated by subtraction of resonance values of UQCRB binding to control biotin from those of UQCRB binding to BT. For competitive binding analysis, the compounds were each incubated with the UQCRB protein, and then the complexes were injected into flow cells of the sensor chip. Consequently, the binding affinity of UQCRB to BT was significantly decreased due to the co-incubation of the compounds and the UQCRB protein, which confirmed that A1893 and A1938 directly bind to UQCRB.

In order to further investigate the binding of A1893 and A1938 to UQCRB, the present inventors performed SPR (BIAcore) analysis. Control biotin and biotinylated terpestacin were sequentially immobilized onto the surface of a streptavidin-coated sensor chip. Competitive binding molecules (A1893 and A1938, 25 μM) were incubated with the purified UQCRB protein (25 μM) in the buffer (10 mM HEPES, 150 mM NaCl, 3 mM EDTA (pH 7.4)), and then UQCRB-competitive binding molecule complexes were injected onto the sensor chip at a flow rate of 30 μl/min. The surface of the sensor chip was regenerated by the injection of 5 μl of the regeneration buffer (50 mM NaOH). Molecular interaction analysis was performed using the BIAcore 2000 system (BIAcore AB), and the apparent binding affinities were calculated by the subtraction of resonance values of UQCRB binding to control biotin from those of UQCRB binding to biotinylated terpestacin. For competitive binding analysis, terpestacin and the compounds of the present invention were each incubated with the UQCRB protein, and then the complexes were injected into flow cells of the sensor chip. Consequently, when terpestacin and the compounds of the present invention were each incubated with the UQCRB protein, the binding efficiency of UQCRB to BT was significantly decreased, which confirmed that A1893 and A1938 directly bind to UQCRB (FIG. 3).

Angiogenesis-Inhibitory Activity Analysis

1. Invasiveness Analysis

Figure 4A:
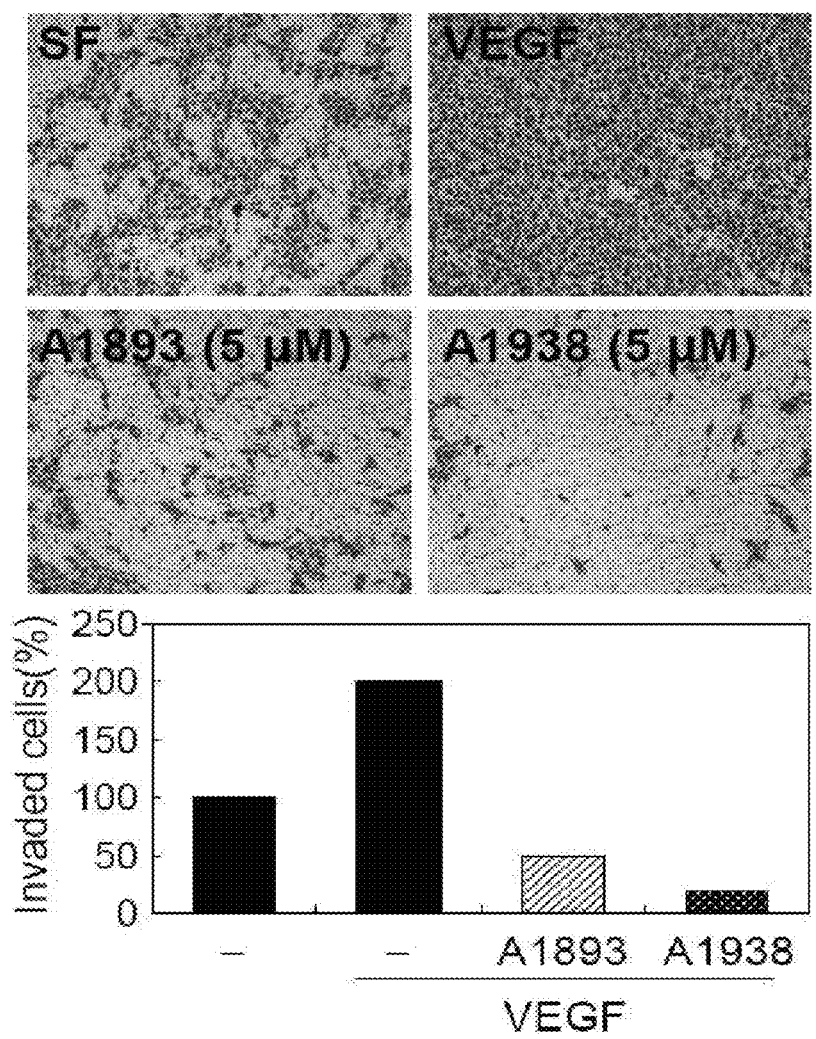
FIG. 4A shows inhibitory activities of A1893 and A1938 on endothelial cell invasion.

Serum-starved human umbilical vein endothelial cells (HUVECs) were treated with VEGF with or without A1893 or A1938, and then the in vitro angiogenesis analysis was performed. The invasiveness of HUVECs was investigated using the Transwell chamber system with 8.0-μm pore-sized polycarbonate filter (Corning Costar). First, a lower portion of the filter was coated with 10 μl gelatin (10 mg/ml) for 1 hour, and an upper portion of the filter was coated with 10 μl Matrigel (3 mg/ml) for 2 hours. Then, 600 μl of the EBM-2 medium was put into the Transwell, and then, VEGF (30 ng/ml) and the compound of the present invention DPCN (2.5 μM and 5 μM) were added thereto. The coated filter was placed on the Transwell, and HUVECs (1×10$^5$ cells/well) were inoculated on the upper portion of the filter, following by incubation for 18 hours. After that, the cells were fixed with 70% methanol, and then stained with hematoxylin/eosin. Then, the total number of invaded cells was measured using an optical microscope at 100× magnification. As a result of the measurement, it was confirmed that A1893 and A1938 inhibited VEGF-induced invasion without affecting viability of endothelial cells (FIG. 4A).

2. Tube Formation Analysis

Figure 4B:
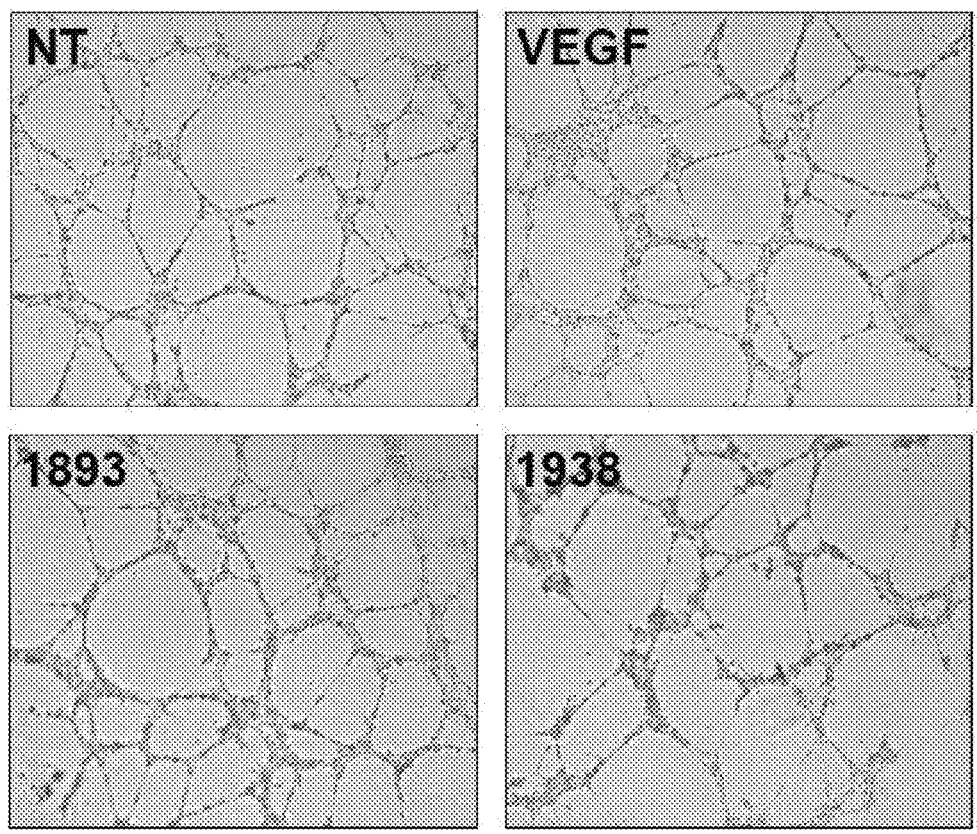
FIG. 4B shows effects of A1893 and A1938 on tube forming ability of HUVECs. A1893 and A1938 inhibited VEGF-induced invasion and tube formation of HUVECs without affecting viability of endothelial cells.

Tube formation analysis was performed using HUVECs growing on Matrigel (Collaborative Biomedical Products). The 48-well plate was coated with 150 μl Matrigel, followed by polymerization at 37 for 2 hours. Then, human umbilical vein endothelial cells (HUVECs, 1×10$^5$ cells/well) were inoculated on Matrigel, and then VEGF (30 ng/ml) and the compound of the present invention DPCN (2.5 μM and 5 μM) were added thereto. The morphological change of cells was observed while the cells were incubated at room temperature for 8 hours. Tube formation was quantified by measuring the number of connected cells in randomly selected fields and dividing the measured number by the total number of cells in the same field. As a result of the measurement, it was confirmed that A1893 and A1938 inhibited the tube formation of HUVECs without affecting viability of endothelial cells (FIG. 4B).

Mitochondrial ROS Generation Analysis

Figure 5:
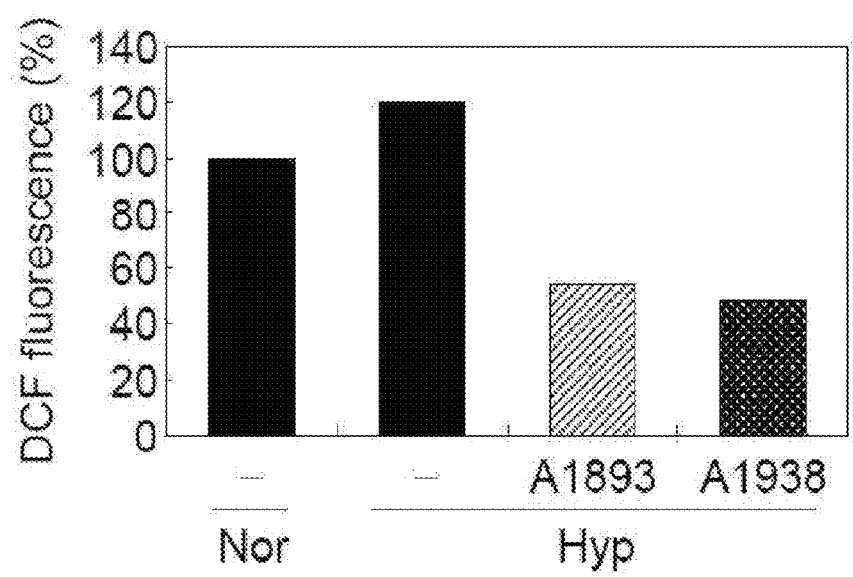
FIG. 5 shows effects of A1893 and A1938 on mitochondrial ROS generation. Intracellular ROS levels were determined by the DCF fluorescence. HepG2 cells were pretreated with the compounds for 30 minutes, and then exposed to 1% $O_2$ for 10 minutes. A1893 and A1938 suppressed hypoxia-induced mitochondrial ROS generation, which confirmed that A1893 and A1938 modulate the $O_2$ sensing function of UQCRB.

The increase in ROS generation due to complex III during hypoxia triggers HIF-1α stabilization, and consequently mediates the expression of its target genes such as VEGF. UQCRB, which is an important component in mitochondrial complex III, acts as an O$_2$ sensor and mediates hypoxia-induced tumor angiogenesis. In order to determine whether anti-angiogenic activity of A1893 and A1938 is associated with the modulation of the O$_2$ sensing function of UQCRB, the present inventors investigated the mitochondrial ROS-mediated hypoxic signal transmission procedure of A1893 and A1938. HepG2 liver cancer cells were pretreated with A1893 and A1938 for 30 minutes, and then exposed to 1% O$_2$ for 10 minutes. Intracellular ROS levels were determined by the DCF fluorescence. A1893 and A1938 suppressed the hypoxia-induced mitochondrial ROS generation in HepG2 cells in a dose-dependent manner (FIG. 5). This result showed that anti-angiogenic activity of A1893 and A1938 is associated with the modulation of the O$_2$ sensing function of UQCRB.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A pharmaceutical composition comprising a compound represented by Chemical Formula 1:

Chemical Formula 1

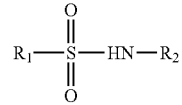

wherein

R₁ is selected from the group consisting of

naphthalyl, and naphthalyl substituted with $C_1$-$C_6$ alkyl;

R₂ is selected from the group consisting of

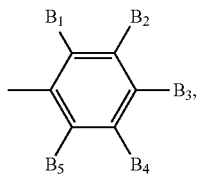

hydroxynaphthalyl, and 4-(2-hydroxyethyl)cyclohexyl;

A₁ is $C_1$-$C_6$ alkyl or phenyl; and

B₁, B₂, B₄, and B₅ are each independently selected from the group consisting of H—, halo, hydroxyl, nitro, and $C_1$-$C_6$ alkyl, and B₃ is selected from the group consisting of H—, halo hydroxyl, and $C_1$-$C_6$ alkyl.

2. The pharmaceutical composition of claim 1, wherein A₁ is methyl, ethyl, phenyl, or tert-butyl.

3. The pharmaceutical composition of claim 1, wherein B₁ is H—, chloro, fluoro, hydroxyl, nitro, or methyl.

4. The pharmaceutical composition of claim 1, wherein the hydroxy naphthalyl is 7-hydroxy naphthalyl.

5. The pharmaceutical composition of claim 1, wherein the compound is selected from the group consisting of:

Chemical Formula 2

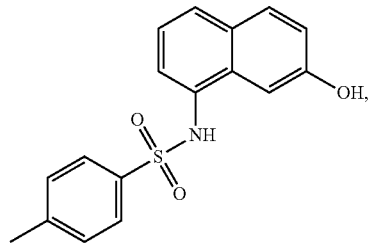

Chemical Formula 3

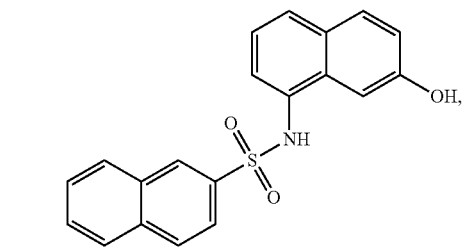

Chemical Formula 4

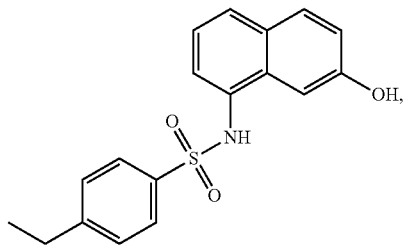

Chemical Formula 5

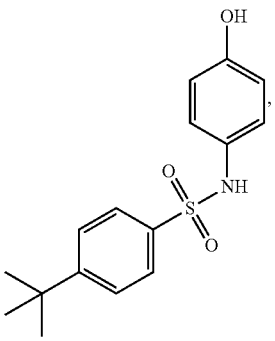

Chemical Formula 6

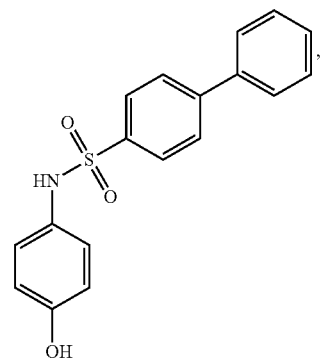

Chemical Formula 10

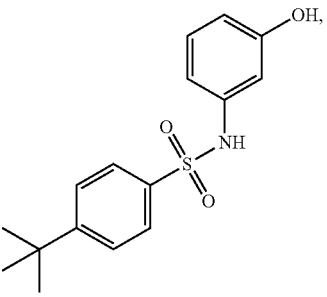

Chemical Formula 11

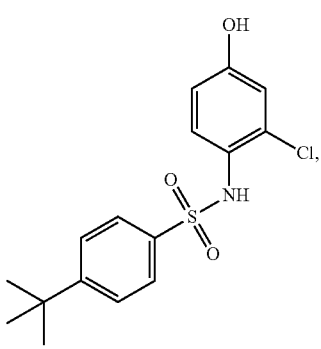

Chemical Formula 12
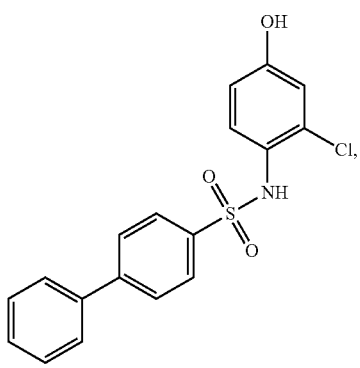
Chemical Formula 13
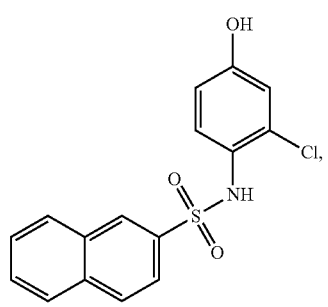
Chemical Formula 14
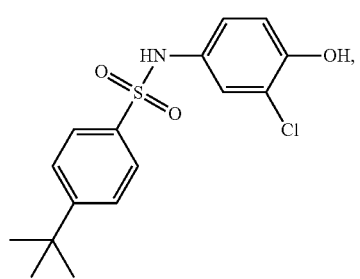
Chemical Formula 15
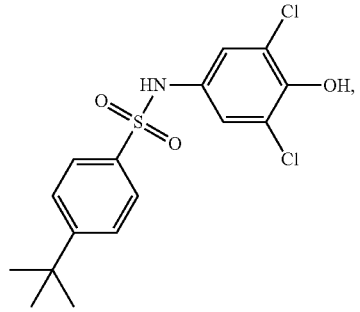
Chemical Formula 16
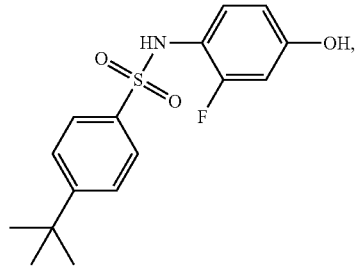
Chemical Formula 17
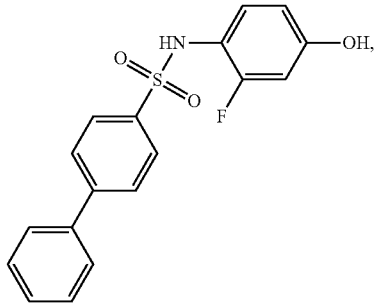
Chemical Formula 18
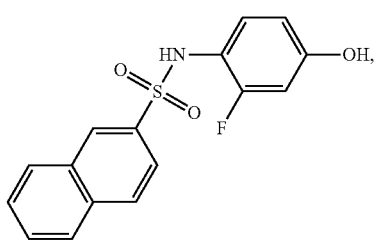
Chemical Formula 19
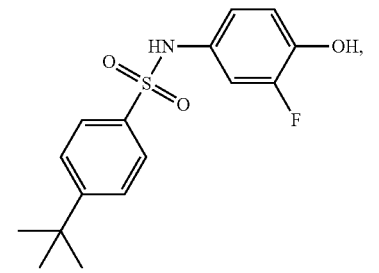
Chemical Formula 20
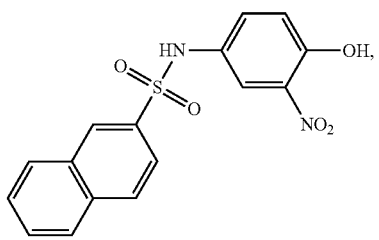
Chemical Formula 21
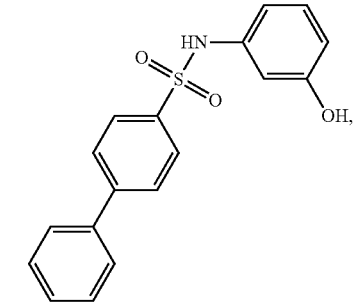
Chemical Formula 22
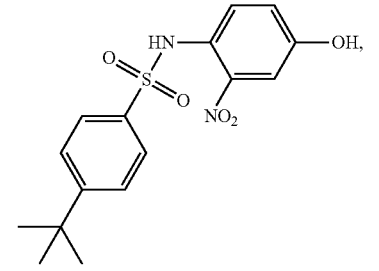

Chemical Formula 23

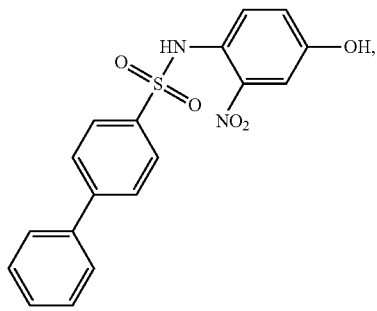

Chemical Formula 24

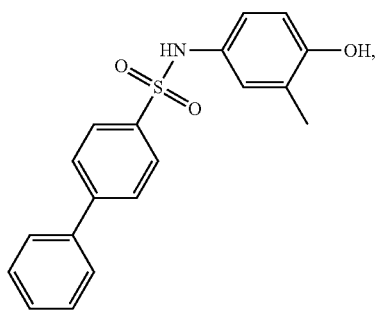

Chemical Formula 25

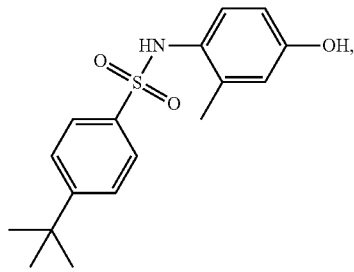

Chemical Formula 26

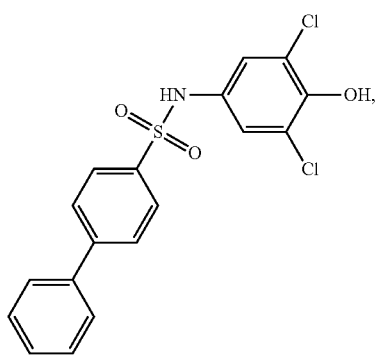

Chemical Formula 27

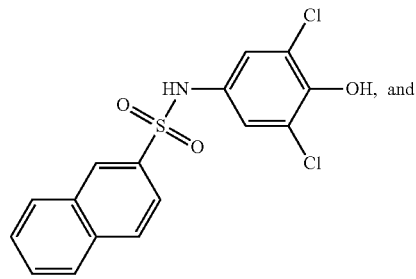

Chemical Formula 29

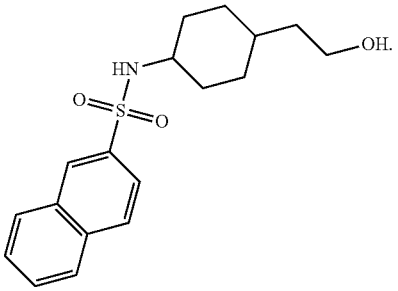

6. The pharmaceutical composition of claim 5, wherein the composition is selected from the group consisting of the compounds represented by Chemical Formulas 5, 6, 12, 17, 21, 23, and 24.

7. A method of treating a disease or disorder selected from the group consisting of cancer, diabetic retinopathy, retinopathy of prematurity, neovascular glaucoma and, proliferative retinopathy, the method comprising:

administering an appropriate dose of the pharmaceutical composition of claim 1 to a subject in need thereof.

8. The method of claim 7, wherein the disease or disorder is a cancer, diabetic retinopathy, or proliferative retinopathy.

9. The method of claim 8, wherein the proliferative retinopathy is age-related macular degeneration.

10. A compound selected from the group consisting of compounds represented by Chemical Formulas 2, 3, 4, 11, 12, 13, 15, 16, 17, 18, 19, 20, 22, 23, 24, 26, and 29:

Chemical Formula 2

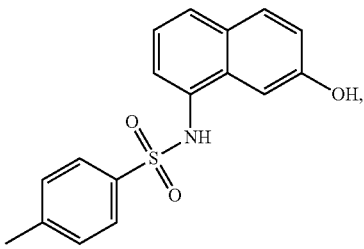

Chemical Formula 3

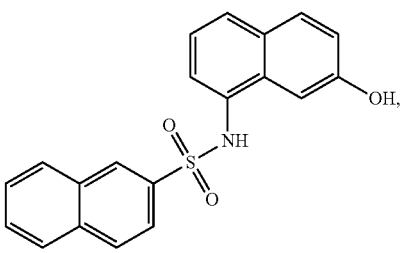

-continued
Chemical Formula 4
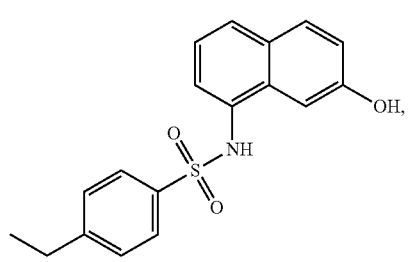
Chemical Formula 11
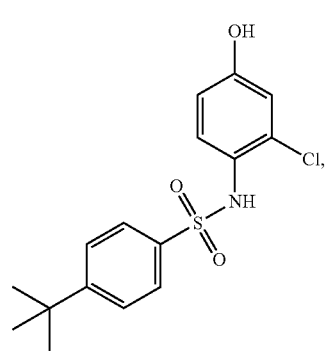
Chemical Formula 12
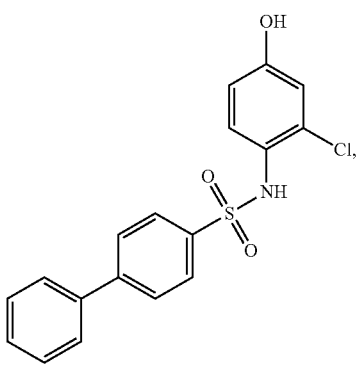
Chemical Formula 13
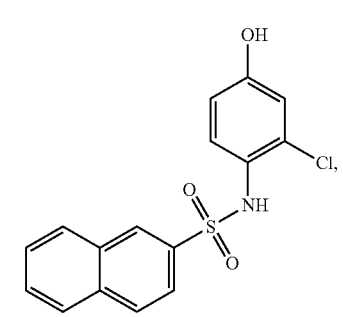
Chemical Formula 15
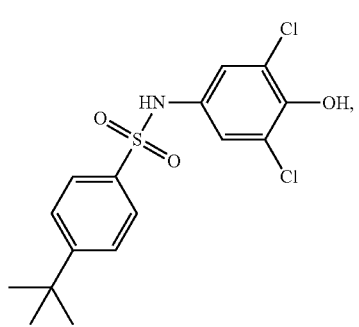
-continued
Chemical Formula 16
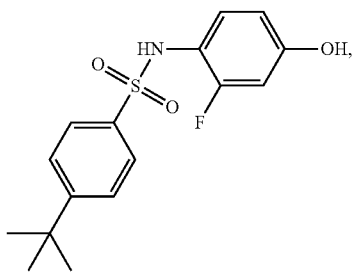
Chemical Formula 17
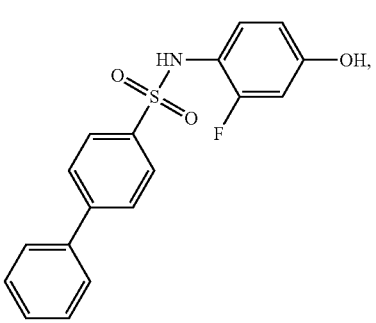
Chemical Formula 18
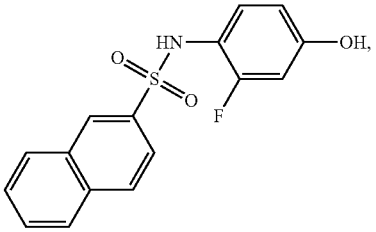
Chemical Formula 19
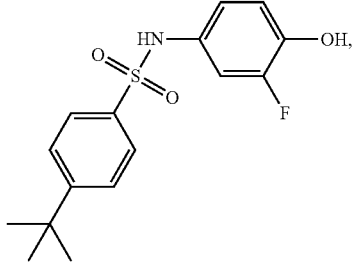
Chemical Formula 20
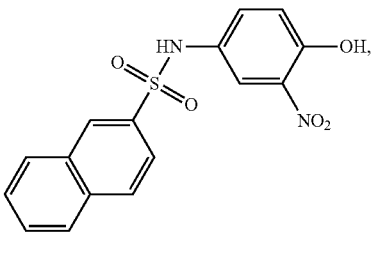

Chemical Formula 22
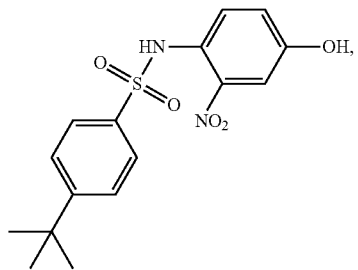
Chemical Formula 23
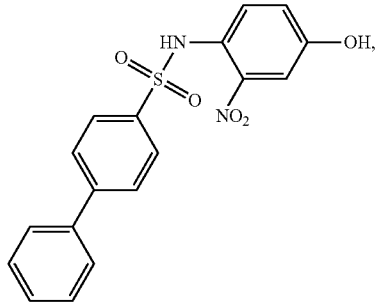
Chemical Formula 24
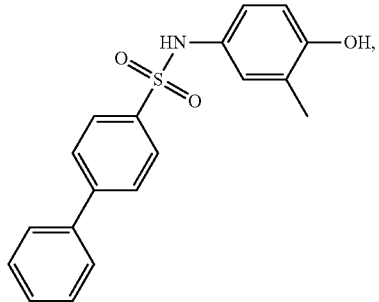
Chemical Formula 26
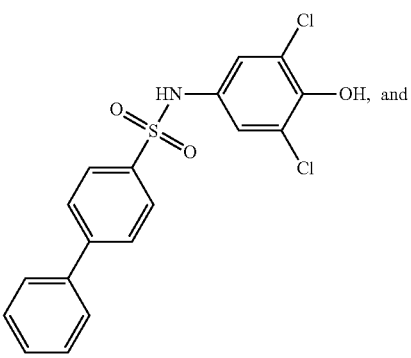
and
Chemical Formula 29
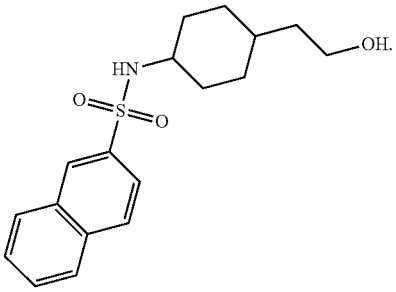
* * * * *